(12) United States Patent
Doerfler et al.

(10) Patent No.: US 11,742,077 B2
(45) Date of Patent: Aug. 29, 2023

(54) SYSTEM AND METHOD FOR CORE-DEVICE MONITORING

(71) Applicant: Medtronic, Inc., Minneapolis, MN (US)

(72) Inventors: John C. Doerfler, West Grove, PA (US); Rodolphe Katra, Blaine, MN (US); Niranjan Chakravarthy, Singapore (SG)

(73) Assignee: Medtronic, Inc., Minneapolis, MN (US)

( * ) Notice: Subject to any disclaimer, the term of this patent is extended or adjusted under 35 U.S.C. 154(b) by 611 days.

(21) Appl. No.: 16/876,768

(22) Filed: May 18, 2020

(65) Prior Publication Data

US 2021/0358606 A1 Nov. 18, 2021

(51) Int. Cl.
*G16H 40/40* (2018.01)

(52) U.S. Cl.
CPC .................... *G16H 40/40* (2018.01)

(58) Field of Classification Search
CPC .................... G16H 40/40; A61N 1/08
See application file for complete search history.

(56) References Cited

U.S. PATENT DOCUMENTS

| 6,584,352 B2 | 6/2003 | Combs et al. |
| 6,804,558 B2 | 10/2004 | Haller et al. |
| 8,396,801 B1 | 3/2013 | Dala et al. |
| 2002/0052539 A1 | 5/2002 | Haller et al. |
| 2004/0064161 A1 | 4/2004 | Gunderson et al. |
| 2005/0137636 A1* | 6/2005 | Gunderson .......... A61N 1/3706 607/27 |
| 2015/0224310 A1 | 8/2015 | Sharma et al. |
| 2018/0161572 A1 | 6/2018 | Gunderson et al. |

FOREIGN PATENT DOCUMENTS

| CN | 108430570 A * | 8/2018 | .......... A61B 5/0022 |
| EP | 1583585 B1 | 6/2008 | |

OTHER PUBLICATIONS

Reiter, M J; Fain, E S; Senelly, K M; Robertson, A D. "Predictors of device activation for ventricular arrhythmias and survival in patients with implantable pacemakers/defibrillators. CADENCE Investigators." Pacing and clinical electrophysiology: PACE17.9: 1487-98. (Sep. 1994) (Year: 1994).*
International Search Report and Written Opinion of International Application No. PCT/US2021/012051, dated Apr. 6, 2021, 8 pp.

* cited by examiner

*Primary Examiner* — Linh Giang Le
(74) *Attorney, Agent, or Firm* — Shumaker & Sieffert, P.A.

(57) ABSTRACT

In some examples, a computing device may receive diagnostic data of a medical device implanted in a patient. The computing device may determine a use case associated with analyzing the diagnostic data out of a plurality of use cases for analyzing the diagnostic data. The computing device may determine, based at least in part on the use case, one or more device characteristics data to be compared against the diagnostic data. The computing device may analyze, based at least in part on comparing the diagnostic data with the one or more device characteristics data, the diagnostic data to determine an operating status of the medical device.

22 Claims, 8 Drawing Sheets

SYSTEM AND METHOD FOR CORE-DEVICE MONITORING

FIELD

This disclosure relates to medical devices, and in some specific examples, relates to computing devices configured to monitor the performance of a medical device that is presently implanted in the patient.

BACKGROUND

Medical devices may be used to monitor and/or treat a variety of medical conditions. Example medical devices include implantable medical devices (IMDs), such as cardiac electronic implantable devices (CEIDs). Such medical devices may be referred to as "core devices." An IMD, also referred to at times as an "implanted medical device," may include a device implanted in a patient at a surgically or procedurally prepared implantation site. An IMD may include a diagnostic device configured to diagnose various ailments of a patient, monitor a health status of the patient, and the like. For example, an IMD may be configured to sense cardiac electrogram (EGM) signals, e.g., electrocardiogram (ECG) signals, indicative of the electrical activity of the heart via electrodes.

An IMD may also be configured to deliver electrical therapy to a patient, e.g., to stimulate the heart, nerves, muscles, brain tissue, etc., via electrodes. In any case, the IMD may, in some instances, include a battery powered component. In such instances, the battery powered component of the IMD may be implanted, such as at a surgically or procedurally prepared implantation site. In addition, associated devices, such as elongated medical electrical leads or drug delivery catheters, can extend from the IMD to other subcutaneous implantation sites or in some instances, deeper into the body, such as to organs or various other implantation sites.

SUMMARY

In general, this disclosure describes techniques for monitoring the operations of core devices such as IMDs to determine the operating status of core devices and/or the physiological status of the patient. In some examples, a computing device may act as a hardware interrogator or programmer for an IMD and may interrogate the IMD for diagnostic data. The computing device or a remote computing system may receive the diagnostic data from the IMD and may perform analysis on the diagnostic data to determine the operating status of the IMD and/or the physiological status of the patient.

The computing device that interrogates the IMD for the diagnostic data may perform on-device analysis of the diagnostic data or may send the diagnostic data to a remote computing system for analysis. The computing device and/or the remote computing system may each provide an analysis platform for technicians to perform manual analysis of the diagnostic data or may perform automatic analysis of the diagnostic data to determine the operating status of the IMD and/or the physiological status of the patient.

In one aspect, the disclosure is directed to a method. The method includes receiving, by processing circuitry of a computing device, diagnostic data of a medical device implanted in a patient. The method further includes determining, by the processing circuitry, a use case associated with analyzing the diagnostic data out of a plurality of use cases for analyzing the diagnostic data. The method further includes determining, by the processing circuitry and based at least in part on the use case, one or more device characteristics data to be compared against the diagnostic data. The method further includes analyzing, by the processing circuitry and based at least in part on comparing the diagnostic data with the one or more device characteristics data, the diagnostic data to determine an operating status of the medical device.

In another aspect, the disclosure is directed to a computing device. The computing device includes memory and processing circuitry in communications with the memory. The processing circuitry is configured to receive diagnostic data of a medical device implanted in a patient; determine a use case associated with analyzing the diagnostic data out of a plurality of use cases for analyzing the diagnostic data; determine, based at least in part on the use case, one or more device characteristics data to be compared against the diagnostic data; and analyze, based at least in part on comparing the diagnostic data with the one or more device characteristics data, the diagnostic data to determine an operating status of the medical device.

In another example, the disclosure is directed to a non-transitory computer-readable medium comprising instructions that, when executed by processing circuitry of a computing system, cause the computing device to: receive diagnostic data of a medical device implanted in a patient; determine a use case associated with analyzing the diagnostic data out of a plurality of use cases for analyzing the diagnostic data; determine, based at least in part on the use case, one or more device characteristics data to be compared against the diagnostic data; and analyze, based at least in part on comparing the diagnostic data with the one or more device characteristics data, the diagnostic data to determine an operating status of the medical device.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

A variety of types of implantable medical devices (IMDs) may sense and monitor cardiac EGMs, and detect arrhythmia or other cardiac episodes. Example IMDs that monitor cardiac EGMs include pacemakers and implantable cardioverter-defibrillators (ICDs), which may be coupled to intravascular or extravascular leads, as well as pacemakers with housings configured for implantation within the heart, which may be leadless. Some IMDs that do not provide therapy, e.g., implantable patient monitors, sense cardiac EGMs. One example of such an IMD is the Reveal LINQ™ Insertable Cardiac Monitor (ICM), available from Medtronic plc, which may be inserted subcutaneously. Such IMDs may facilitate relatively longer-term monitoring of patients during normal daily activities, and may periodically transmit collected data, such as diagnostic data regarding the status of various components of the IMD as well as physiological data such cardiac EGMs to a remote patient monitoring system, such as the Medtronic Carelink™ Network.

In order to determine whether an IMD is operating normally (e.g., within normal operating parameters), the IMD may be periodically interrogated for diagnostic data by a computing device that acts as a hardware interrogator/programmer such as the Medtronic 2090 programmer, or another specialized or commercial mobile computing device. The computing device may receive the diagnostic data from the IMD and may, in some instances, provide an analysis platform for manual and/or automated analysis of the diagnostic data to determine the operating status of the IMD and/or the physiological status of the patient. In other examples, the computing device may receive the diagnostic data from the IMD and may send the diagnostic data to a remote computing system that may provide an analysis platform for manual and/or automated analysis of the diagnostic data to determine the operating status of the IMD and/or the physiological status of the patient.

Figure 1:
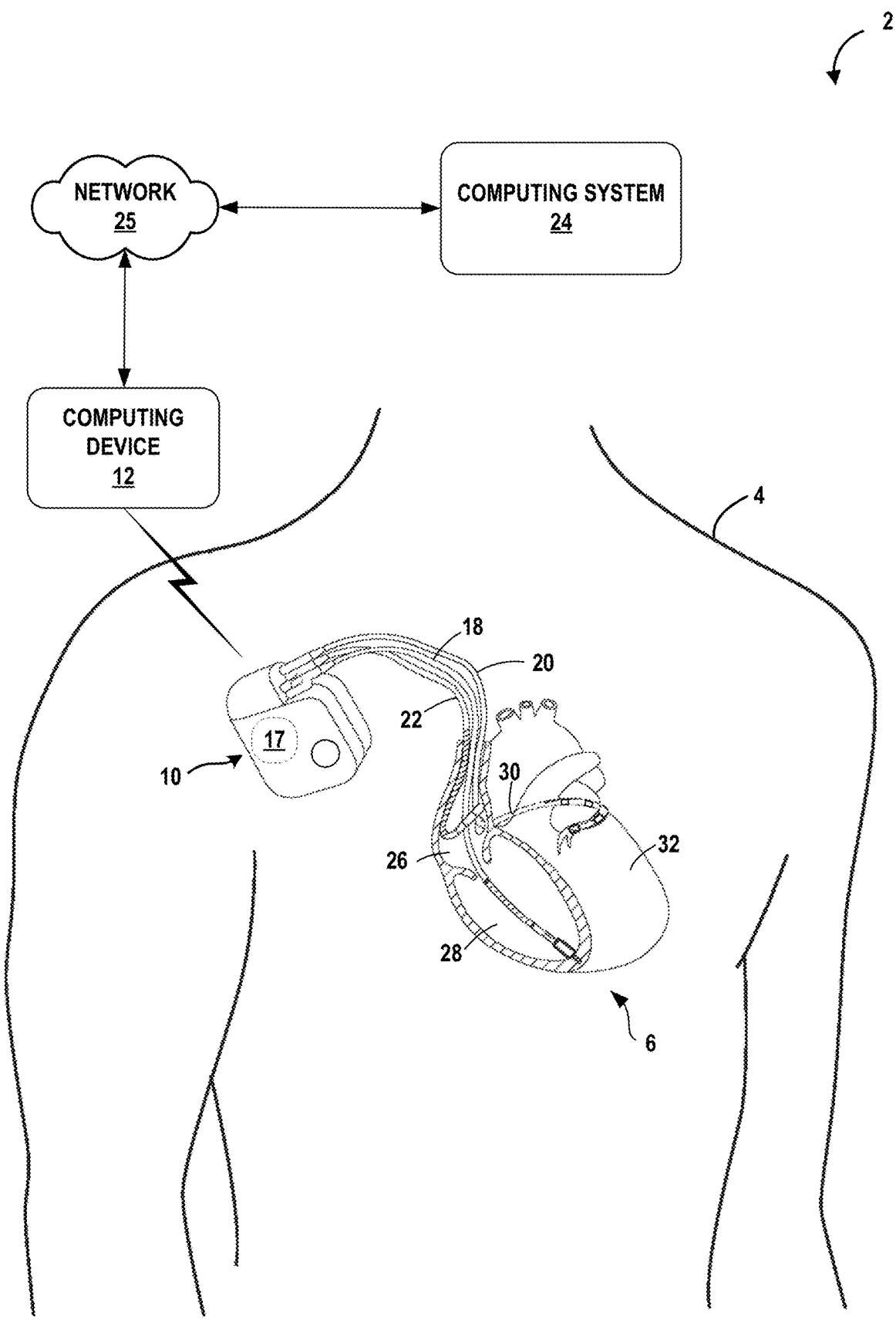
FIG. 1 is a conceptual drawing illustrating an example of a medical device system configured to at least one of monitor or deliver therapy to a patient.

FIG. 1 illustrates the environment of an example medical device monitoring system 2 in conjunction with a patient 4, in accordance with the techniques of the disclosure. In some examples, system 2 may implement the various patient and medical device monitoring techniques disclosed herein. As shown in FIG. 1, system 2 includes one or more medical device(s), such as IMD 10, one or more computing device(s), such as computing device 12, and one or more computing system(s), such as computing system 24, that may communicate with computing device 12 via network 25.

As illustrated by example system 2 in FIG. 1, IMD 10 may, in some examples, be an implantable cardiac pacemaker, implantable cardioverter/defibrillator (ICD), or pacemaker/cardioverter/defibrillator, for example. IMD 10 is connected to leads 18, 20 and 22. IMD 10 is communicatively coupled, e.g., capable of being selectively communicatively coupled, to computing device 12. Although not illustrated in FIG. 1, computing device 12 may be communicatively coupled to one or more computing devices over a communication network.

IMD 10 senses electrical signals attendant to the depolarization and repolarization of heart 6, e.g., a cardiac electrogram (EGM), via electrodes on one or more leads 18, 20 and 22 or the housing of IMD 10. IMD 10 may also deliver therapy in the form of electrical signals to heart 6 via electrodes located on one or more leads 18, 20 and 22 or a housing of IMD 10. The therapy may be pacing, cardioversion and/or defibrillation pulses. IMD 10 may monitor EGM signals collected by electrodes on leads 18, 20 or 22, and based on the EGM signal, diagnose, and treat cardiac episodes, such as tachyarrhythmias.

In some examples, IMD 10 includes communication circuitry 17 including any suitable circuitry, firmware, software, or any combination thereof for communicating with another device, such as computing device 12 of FIG. 1. For example, communication circuitry 17 may include one or more processors, memory, wireless radios, antennae, transmitters, receivers, modulation and demodulation circuitry, filters, amplifiers, or the like for radio frequency communication with other devices, such as computing system 24. IMD 10 may use communication circuitry 17 to receive downlinked data from to control one or more operations of IMD 10 and/or send uplinked data to computing device 12.

Leads 18, 20, 22 extend into the heart 6 of patient 4 to sense electrical activity of heart 6 and/or deliver electrical stimulation to heart 6. In the example shown in FIG. 1, right ventricular (RV) lead 18 extends through one or more veins (not shown), the superior vena cava (not shown), and right atrium 26, and into right ventricle 28. Left ventricular (LV) lead 20 extends through one or more veins, the vena cava, right atrium 26, and into the coronary sinus 30 to a region adjacent to the free wall of left ventricle 32 of heart 6. Right atrial (RA) lead 22 extends through one or more veins and the vena cava, and into the right atrium 26 of heart 6.

While example system 2 of FIG. 1 depicts IMD 10, in other examples, the techniques of the disclosure may be applied to other types of medical devices that are not necessarily implantable. For example, a medical device in accordance with the techniques of the disclosure may include a wearable medical device or "smart" apparel worn by patient 4. For example, such a medical device may take the form of a wristwatch worn by patient 4, circuitry that is adhesively affixed to patient 4, or a wearable automated external defibrillator (WAED). In another example, a medical device as described herein may include an external medical device with implantable electrodes.

In some examples, computing device 12, which is external to patient 4, takes the form of an external programmer or mobile device, such as a mobile phone, a "smart" phone, a laptop, a tablet computer, a personal digital assistant (PDA), a wearable electronic device, a handheld computing device, computer workstation, server or other networked computing device, etc. In some examples, computing device 12 is a CareLink™ monitor available from Medtronic, Inc. While depicted as a single device in the example of FIG. 1, in some examples, computing device 12 comprises one or more computing devices that implement a remote monitoring or remote care system. A user, such as a physician, technician, surgeon, electro-physiologist, or other clinician, may interact with computing device 12 to retrieve physiological or diagnostic information from IMD 10. A user, such as patient 4 or a clinician as described above, may also interact with computing device 12 to program IMD 10, e.g., select or adjust values for operational parameters of IMD 10. Computing device 12 may include processing circuitry, a memory, a user interface, and communication circuitry capable of transmitting and receiving information to and from each of IMD 10 and computing system 24.

IMD 10 and computing device 12 may communicate via wireless communication using any techniques known in the art. Examples of communication techniques may include, for example, include radiofrequency (RF) telemetry, which may be an RF link established via an antenna according to Bluetooth® or Bluetooth® Low Energy (BLE)®, WiFi, or medical implant communication service (MICS), though other techniques are also contemplated. In some examples, computing device 12 may include a programming head that may be placed proximate to the patient's body near the IMD 10 implant site in order to improve the quality or security of communication between IMD 10 and computing device 12.

Computing device 12 may also be configured to communicate with computing system 24 via network 25. Computing system 24 may comprise computing devices configured to allow a user to interact with IMD 10, or data collected from IMD 10, via network 25. For example, computing system 24 may include one or more handheld computing devices, computer workstations, servers or other networked computing devices. In some examples, computing system 24, network 25, and computing device 12 may be implemented by the Medtronic Carelink™ Network or other patient monitoring system.

Network 25 may include one or more computing devices (not shown), such as one or more non-edge switches, routers, hubs, gateways, security devices such as firewalls, intrusion detection, and/or intrusion prevention devices, servers, computer terminals, laptops, printers, databases, wireless mobile devices such as cellular phones or personal digital assistants, wireless access points, bridges, cable modems, application accelerators, or other network devices. Network 25 may include one or more networks administered by service providers, and may thus form part of a large-scale public network infrastructure, e.g., the Internet. Network 25 may provide computing devices, such as computing device 12, computing system 24, and IMD 10, access to the Internet, and may provide a communication framework that allows the computing devices to communicate with one another. In some examples, network 25 may be a private network that provides a communication framework that allows computing system 24, IMD 10, and/or computing device 12 to communicate with one another but isolates one or more of computing system 24, IMD 10, or computing device 12 from devices external to network 25 for security purposes. In some examples, the communications between computing system 24, IMD 10, and computing device 12 are encrypted.

Computing device 12 may be used to interrogate IMD 10 to obtain diagnostic data from IMD 10. Examples of diagnostic data include performance data of IMD 10, historical data stored to memory of IMD 10, battery status of IMD 10 such as the remaining longevity of the battery, status of therapy-delivery leads of IMD 10 such as lead impedance, sensing level of IMD 10, such as the ability of IMD 10 to sense R-waves using the electrodes carried by its leads, thresholds for therapy capture, pulse width, pacing percentage, pulse amplitude, pacing mode, pacing level changes, internal device temperature, fluid status monitored by IMD 10, and the like, as well as physiological parameters measured by IMD 10, indications of episodes of arrhythmia or other maladies detected by IMD 10, episode data collected for episodes, and other physiological signals recorded by IMD 10. Such diagnostic data obtained from IMD 10 may be used to perform device diagnostics of IMD 10 as well as patient diagnostics of patient 4.

In some examples, computing device 12 may interrogate IMD 10 to obtain diagnostic data from IMD 10. To interrogate IMD 10, computing device 12 may communicate with IMD 10 via a wireless connection, such as RFID, Bluetooth®, Wi-Fi™, NFC, and the like, to send a request for diagnostic data to IMD 10. In response to receiving the request from computing device 12, IMD 10 may send the current up-to-date diagnostic data of IMD 10 to computing device 12 via the wireless connection. Computing device 12 may therefore receive the diagnostic data sent by IMD 10.

In some examples, computing device 12 may interrogate IMD 10 in response to computing device 12 being in sufficient physical proximity to IMD 10 (e.g., within a specified physical distance such as within 6 inches or 6 feet from IMD 10). Computing device 12 and/or IMD 10 may determine whether they are in proximity to each other via any suitable technique. In some examples, computing device 12 and IMD 10 may determine whether they are in sufficient proximity to each other via inductive coupling (e.g., NFC). In some examples, computing device 12 may determine that it is in sufficient proximity to IMD 10 based on the signal strength of its wireless connection to IMD 10 or based on detection of advertisement signals from IMD 10. For example, after patient 4 is discharged from the hospital after implantation of IMD 10, computing device 12 may be a bedside monitor that may interrogate IMD 10 for diagnostic data each time patient 4 is near (e.g., walks by) computing device 12.

In some examples, computing device 12 may include a programming head or paddle (not shown). In such examples, computing device 12 may interface with IMD 10 via the programming head so that computing device 12 may, in response to the programming head may be placed proximate to the body of patient 4 near IMD 10 (e.g., near an implantation site of IMD 10), interrogate IMD 10.

In some examples, computing device 12 and IMD 10 may communicate so that IMD 10 may regularly send diagnostic data to computing device 12. Computing device 12 may interrogate IMD 10 at regular intervals and IMD 10 may, in response to being interrogated, send diagnostic data to computing device 12. For example, computing device 12 may be set to a "post-surgery" mode where computing device 12 may regularly interrogate IMD 10 over a number of days post-implantation of IMD 10, such as interrogating IMD 10 every six hours for up to four days post-surgery.

Computing device 12 may analyze the diagnostic data received from IMD 10 and/or send the diagnostic data to computing system 24 for analysis. In some examples, even when computing device 12 performs analysis of the diagnostic data, computing device 12 may sync the diagnostic data and/or the results of analyzing the diagnostic data to computing system 24.

In some examples, computing device 12 may provide an analysis platform for performing manual and/or automated analysis of the diagnostic data received from IMD 10, so that computing device 12 may perform on-device analysis of the diagnostic data. The analysis platform of computing device 12 enables users (e.g., trained technicians, physicians, fellows, nurse practitioners, etc.) to manually perform analysis of the diagnostic data and to generate a report of such analysis, such as by printing a copy of the report. For example, computing device 12 may present the received diagnostic data in a user interface with which one or more users may interact in order to analyze the diagnostic data to determine the operating status of IMD 10 and/or the health status of patient 4.

Computing device 12 may therefore be able to perform analysis of the diagnostic data without having a network connection (e.g., without being connected to network 25 or to other networks), which may potentially be useful in settings such as hospitals where it may be challenging for computing device 12 to connect to communication infrastructure such as network 25. Once computing device 12 has finished analysis of the diagnostic data, computing device 12 may save the results of the analysis into memory or a storage device of computing device 12 and may sync (e.g., upload) the results of the analysis along with the received diagnostic data to computing system 24.

In some examples, computing device 12 may send the diagnostic data received from IMD 10 to a remote system, such as computing system 24, that may provide a remote analysis platform for remote users to manually perform analysis of the diagnostic data. By sending the diagnostic data to computing system 24 for analysis, computing device 12 may enable users such as trained technicians, physicians, fellows, nurse practitioners, and the like to perform analysis of the diagnostic data without being physically proximate to computing device 12 and patient 4.

Enabling such remote users to perform analysis of the diagnostic data may potentially be more convenient to patient 4 as remote users may be able to analyze the diagnostic data of IMD 10 without having patient 4 travel to a hospital or clinic for regular follow-ups, so that patient 4 may only have to visit the clinic for exception-based follow-ups. Enabling such remote users to perform analysis of the diagnostic data may also potentially be more convenient for remote users as the remote users may not have to travel to meet patient 4 in order to analyze the diagnostic data of IMD 10. Further, enabling such remote users to perform analysis of the diagnostic data may also increase the scalability of patient monitoring by enabling a relatively small number of users to remote perform analysis for a relatively large number of patients.

In some examples, in response to receiving the diagnostic data from IMD 10, computing device 12 and/or computing system 24 may analyze the diagnostic data received from IMD 10 to determine the operating status of IMD 10 and/or the health status of patient 4. That is, instead of having users manually perform analysis of the diagnostic data, computing device 12 and/or computing system 24 may be able to analyze the diagnostic data received from IMD 10 to determine the operating status of IMD 10 and/or the health status of patient 4. Computing device 12 may perform on-device analysis of the diagnostic data from IMD 10 or may send the diagnostic data from IMD 10 to computing system 24 for analysis.

Computing device 12 and/or computing system 24 may analyze the diagnostic data transmitted by IMD 10 to determine whether IMD 10 is operating normally and/or to determine the health status of patient 4. To determine whether IMD 10 is operating normally, computing device 12 and/or computing system 24 determine whether each of one or more parameters values associated with the operations of IMD 10 specified by the diagnostic data falls within an acceptable range of values associated with IMD 10 operating normally. For example, if the diagnostic data specifies a lead impedance value, computing device 12 and/or computing system 24 may determine an acceptable range of values for lead impedance. Computing device 12 and/or computing system 24 may determine whether the lead impedance value specified by the diagnostic data falls within an acceptable range of values for lead impedance during normal operations of IMD 10.

Similarly, to determine the patient status of patient 4, computing device 12 and/or computing system 24 determine whether each of one or more parameters values associated with the status of patient 4 specified by the diagnostic data falls within an acceptable range of values. For example, if the diagnostic data specifies ECG values for patient 4 measured by IMD 10, computing device 12 and/or computing system 24 may determine whether patient 4 is experiencing, for example, arrhythmia, based at least in part on the ECG values for patient 4 specified by the diagnostic data.

In some examples, computing device 12 and/or computing system 24 may compare the diagnostic data against device characteristics data to determine whether IMD is operating normally. Device characteristics data may be data regarding the device characteristics of implantable medical devices similar to IMD 10, such as implantable medical devices that are the same type, the same brand and/or model of IMD as IMD 10, under normal operation.

In some examples, device characteristics data may be derived from engineering testing of IMDs, bench testing of IMDs and/or clinical studies of similar IMDs. The device characteristics data may also be data collected from a population of similar IMDs in operation over time, such as from a plurality of medical devices implanted in a plurality of patients. The device characteristics data may also include a history of diagnostic data previously collected by IMD 10 during operations and sent by IMD 10 to computing device 12.

Computing device 12 and/or computing system 24 may analyze diagnostic data received from IMD 10 to check the operating status of IMD 10 and/or the health status of patient 4 in a variety of different situations. These situations are referred to herein as use cases.

In a first use case, shortly after IMD 10 has been implanted in patient 4, such as while patient 4 is in the hospital recovering from surgery, computing device 12 and/or computing system 24 may be used to analyze diagnostic data from IMD 10 to determine whether there are any issues with the implantation of IMD 10. This use case may be referred to as a next-day follow-up monitoring, as computing device 12 may, in this use case, interrogate IMD 10 the day after the surgery to implant IMD 10 in order to determine whether there are any issues with IMD 10. In this use case, computing device 12 and/or computing system 24 may determine whether IMD 10 has remained in place since surgery and whether IMD 10 is operating normally.

In another use case, patient 4 may undergo routine follow-up monitoring once patient 4 has been discharged from the hospital after surgery to implant IMD 10. Such routine follow-up may occur periodically, such as every two weeks for the first six months after surgery, twice a year (i.e., once every six months), once a year, and the like. During a routine follow-up of patient 4, computing device 12 and/or computing system 24 may analyze diagnostic data received from IMD 10 to determine whether IMD 10 is operating normally and to determine the health status of patient 4.

In another use case, computing device 12 and/or computing system 24 may be used to perform exception-based follow-up monitoring on patient 4 after implantation of IMD 10. For example, computing device 12 may receive diagnostic data from IMD 10 that includes one or more values that are outside an acceptable range of values. In this case, computing device 12 and/or computing system 24 may determine that a possible exception has occurred. Exception-based follow-up monitoring may also occur during any other emergency healthcare visits by patient 4 to a hospital or clinic, such as visits to an emergency room or to an urgent care clinic. In this use case, in response to determining that a possible exception has occurred at IMD 10, computing device 12 and/or computing system 24 may analyze diagnostic data received from IMD 10 to determine whether IMD 10 is operating normally and to determine the health status of patient 4.

Computing device 12 and/or computing system 24 may determine, based at least in part on the use case, the one or more device characteristics data to be compared against the diagnostic data to determine whether IMD 10 is operating normally and/or to determine the health status of IMDs. For example, in the next day use case where the diagnostic data from IMD 10 is analyzed the day after implantation of IMD 10, IMD 10 may not have a history of diagnostic data previously collected by IMD 10 during operations that may be used as device characteristics data to determine the operating status of IMD 10. Thus, for the next day use case, computing device 12 and/or computing system 24 may select device characteristics data derived from engineering testing of IMDs, bench testing of IMDs and/or clinical studies of similar IMDs for determining the operating status of IMD 10.

In accordance with the techniques of this disclosure, computing device 12 and/or computing system 24 may receive data of IMD 10 implanted in patient 4. Computing device 12 and/or computing system 24 may determine a use case associated with analyzing the diagnostic data out of a plurality of use cases for analyzing the diagnostic data. Computing device 12 and/or computing system 24 may determine, based at least in part on the use case, one or more device characteristics data to be compared against the diagnostic data. Computing device 12 and/or computing system 24 may analyze, based at least in part on comparing the diagnostic data with the one or more device characteristics data, the diagnostic data to determine an operating status of IMD 10.

The techniques of the disclosure may provide certain advantages. For example, aspects of the disclosure enables an interrogating device, such as computing device 12 to interrogate IMD 10 for diagnostic data and to perform on-device analysis of the diagnostic data without sending the diagnostic data to a remote server for analysis, thereby enabling analysis of the diagnostic data even when the interrogating device is unable to establish a network connection (e.g., a cellular or Wi-Fi connection).

In another example, aspects of the disclosure may be able to adapt the analysis of the diagnostic data depending on the use case for analyzing the diagnostic data by determining the specific device characteristics data to which the diagnostic data is compared in order to analyze the diagnostic data. By determining the specific device characteristics data used to analyze the diagnostic data based on the use case, aspects of the disclosure reduces the amount of processing cycles that may be wasted to analyze the diagnostic data against device characteristics data that may not be relevant to the current use case, thereby enabling the diagnostic data of IMD 10 to be analyzed using fewer processing cycles.

Figure 2:
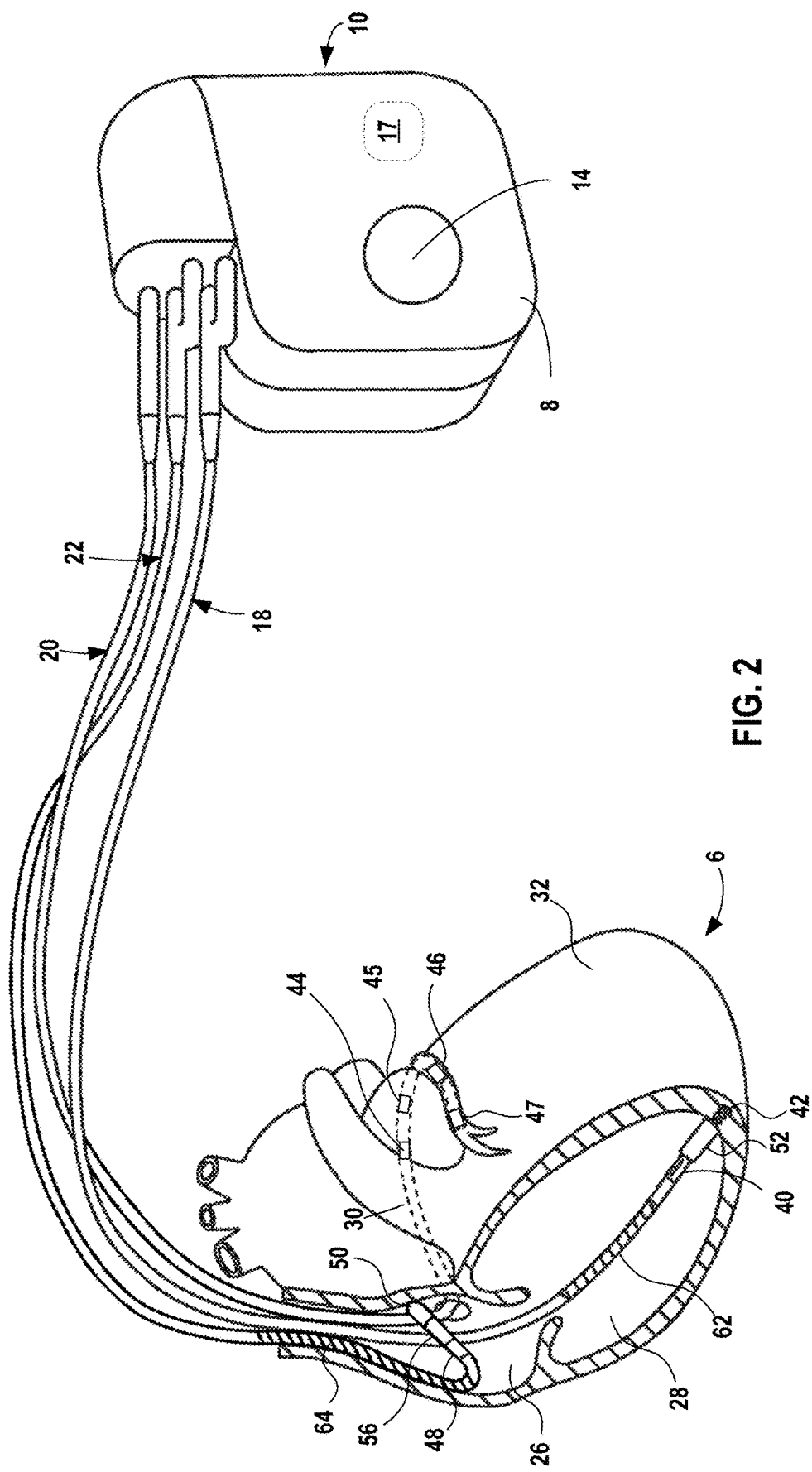
FIG. 2 is a conceptual diagram illustrating the IMD and leads of the system of FIG. 1 in greater detail.

FIG. 2 is a conceptual diagram illustrating IMD 10 and leads 18, 20, 22 of system 2 of FIG. 1 in greater detail. In the illustrated example, bipolar electrodes 40 and 42 are located adjacent to a distal end of lead 18, and bipolar electrodes 48 and 50 are located adjacent to a distal end of lead 22. In addition, four electrodes 44, 45, 46 and 47 are located adjacent to a distal end of lead 20. Lead 20 may be referred to as a quadrapolar LV lead. In other examples, lead 20 may include more or fewer electrodes. In some examples, LV lead 20 comprises segmented electrodes, e.g., in which each of a plurality of longitudinal electrode positions of the lead, such as the positions of electrodes 44, 45, 46 and 47, includes a plurality of discrete electrodes arranged at respective circumferential positions around the circumference of lead.

In the illustrated example, electrodes 40 and 44-48 take the form of ring electrodes, and electrodes 42 and 50 may take the form of extendable helix tip electrodes mounted retractably within insulative electrode heads 52 and 56, respectively. In some examples, each of electrodes 40, 42, 44-48, and 50 is electrically coupled to a respective conductor within the lead body of its associated lead 18, 20, 22 and thereby coupled to circuitry within IMD 10.

In some examples, IMD 10 includes one or more housing electrodes, such as housing electrode 14 illustrated in FIG. 2, which may be formed integrally with an outer surface of hermetically-sealed housing 8 of IMD 10 or otherwise coupled to housing 8. In some examples, housing electrode 14 is defined by an uninsulated portion of an outward facing portion of housing 8 of IMD 10. Other divisions between insulated and uninsulated portions of housing 8 may be employed to define two or more housing electrodes. In some examples, a housing electrode comprises substantially all of housing 8.

Housing 8 encloses signal generation circuitry that generates therapeutic signals, such as cardiac pacing, cardioversion, and defibrillation pulses, as well as sensing circuitry for sensing electrical signals attendant to the depolarization and repolarization of heart 6. Housing 8 may also enclose a memory for storing the sensed electrical signals. Housing 8 may also enclose a communication circuitry 17 for communication between IMD 10 and computing system 24.

IMD 10 senses electrical signals attendant to the depolarization and repolarization of heart 6 via electrodes 14, 40, 42, 44-48, and 50. IMD 10 may sense such electrical signals via any bipolar combination of electrodes 40, 42, 44-48, and 50. Furthermore, any of the electrodes 40, 42, 44-48, and 50 may be used for unipolar sensing in combination with housing electrode 14.

The illustrated numbers and configurations of leads 18, 20 and 22 and electrodes are merely examples. Other configurations, i.e., number and position of leads and electrodes, are possible. In some examples, system 2 may include an additional lead or lead segment having one or more electrodes positioned at different locations in the cardiovascular system for sensing and/or delivering therapy to patient 4. For example, instead of or in addition to intracardiac leads 18, 20 and 22, system 2 may include one or more epicardial or extravascular (e.g., subcutaneous or substernal) leads not positioned within heart 6.

Although described herein in the context of example IMD 10 that provides electrical therapy, the techniques disclosed herein may be used with other types of devices. For example, the techniques may be implemented with one or more of an extra-cardiac defibrillator coupled to electrodes outside of the heart or outside of the cardiovascular system, a transcatheter pacemaker configured for implantation within the heart, such as the Micra™ transcatheter pacing system commercially available from Medtronic, Inc., Minneapolis, Minn., an insertable cardiac monitor, such as the Reveal LINQ™ ICM, also commercially available from Medtronic, Inc., a neurostimulator, a drug delivery device, a wearable device such as a wearable cardioverter defibrillator, a fitness tracker, or other wearable device, a mobile device, such as a mobile phone, a "smart" phone, a laptop, a tablet computer, a personal digital assistant (PDA), or "smart" apparel such as "smart" glasses or a "smart" watch.

Figure 3:
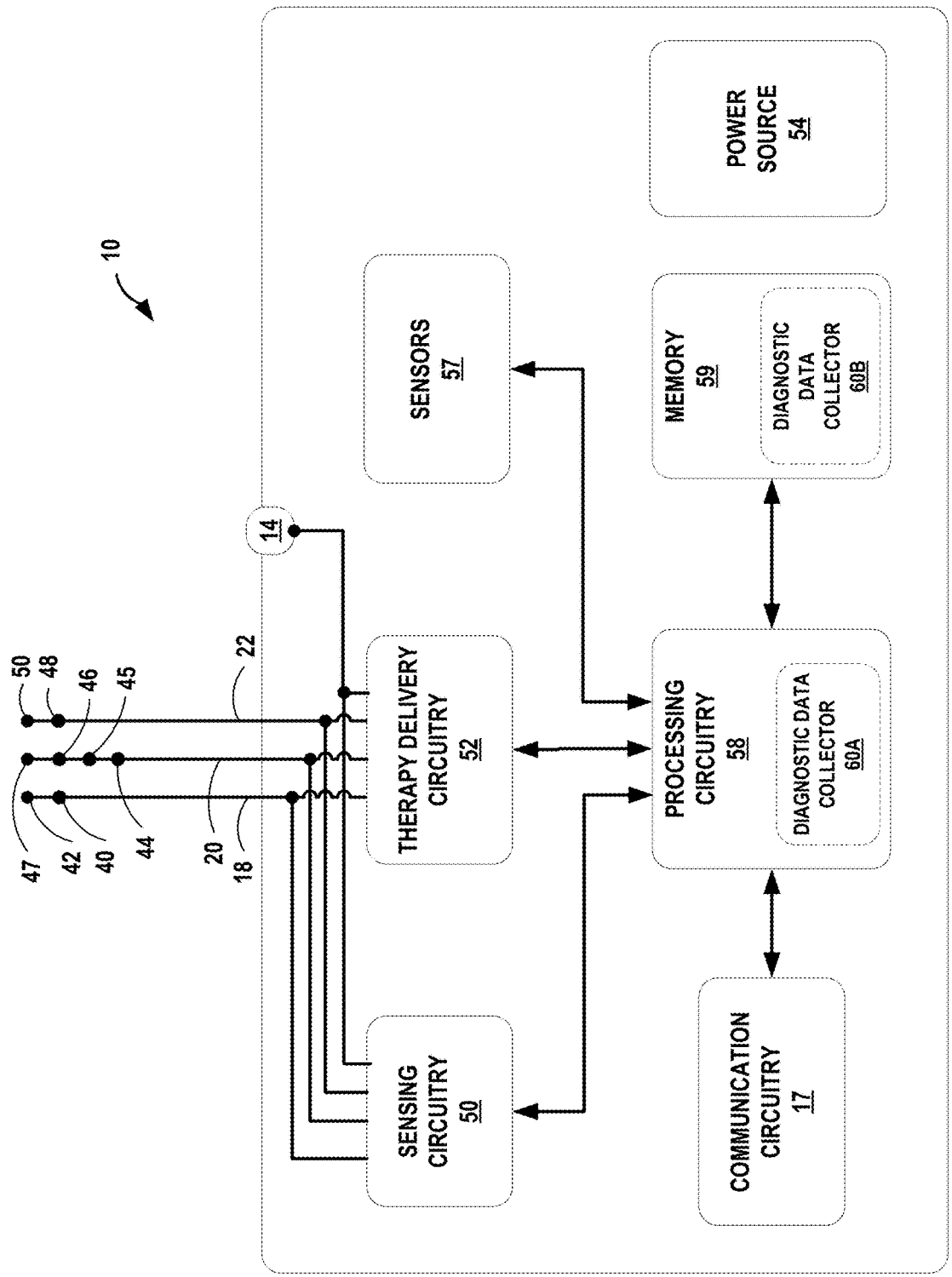
FIG. 3 is a block diagram of example configuration of the IMD of FIGS. 1 and 2 according to the techniques of the disclosure.

FIG. 3 is a block diagram of example configuration of IMD 10 according to the techniques of the disclosure. In the illustrated example, IMD 10 includes processing circuitry 58, memory 59, communication circuitry 17, sensing circuitry 50, therapy delivery circuitry 52, sensors 57, and power source 54. Memory 59 includes computer-readable instructions that, when executed by processing circuitry 58, cause IMD 10 and processing circuitry 58 to perform various functions attributed to IMD 10 and processing circuitry 58 herein (e.g., performing cardiac arrhythmia detection and delivering therapy, such as anti-tachycardia pacing, bradycardia pacing, and post-shock pacing therapy, determining diagnostic data, etc.). Memory 59 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 58 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 58 may include multiple components, such as any combination of one or more microprocessors, one or more controllers, one or more DSPs, one or more ASICs, or one or more FPGAs, as well as other discrete or integrated logic circuitry. The functions attributed to processing circuitry 58 herein may be embodied as software, firmware, hardware or any combination thereof.

Processing circuitry 58 controls therapy delivery circuitry 52 to deliver therapy to heart 6 according to therapy parameters, which may be stored in memory 59. For example, processing circuitry 58 may control therapy delivery circuitry 52 to deliver electrical pulses with the amplitudes, pulse widths, frequency, or electrode polarities specified by the therapy parameters. In this manner, therapy delivery circuitry 52 may deliver pacing pulses (e.g., ATP pulses, bradycardia pacing pulses, or post-shock pacing therapy) to heart 6 via one or more of electrodes 14, 40, 42, 44-48, and 50. In some examples, therapy delivery circuitry 52 may deliver pacing stimulation, e.g., ATP therapy, bradycardia therapy, or post-shock pacing therapy, in the form of voltage or current electrical pulses. In other examples, therapy delivery circuitry 52 may deliver one or more of these types of stimulation in the form of other signals, such as sine waves, square waves, or other substantially continuous time signals.

In some examples, processing circuitry 58 may implement diagnostic data collector 60A stored by memory 59 as diagnostic data collector (collectively, diagnostic data collector 60). Processing circuitry 58 executes diagnostic data collector 60 to determine diagnostic data such as activity level of the patient, a heart rate of the patient, a posture of the patient, a cardiac electrogram of the patient, a blood pressure of the patient, accelerometer data for the patient, or other physiological data for the patient, as well as the status of various components of IMD 10, such as the battery status (e.g., battery level, remaining battery lifetime, etc. of power source 54), impedance of leads 18, 20, and 22, as well as other information such as R-waves using the electrodes 14, 40, 42, 44-48, and 50 carried by its leads 18, 20, and 22, thresholds for therapy capture, pulse width, pacing percentage, pulse amplitude, pacing mode, pacing level changes, internal device temperature, fluid status monitored by IMD 10, and the like.

Therapy delivery circuitry 52 is electrically coupled to electrodes 14, 40, 42, 44-48, and 50. In other examples, IMD 10 may utilize other numbers of electrodes not depicted in FIG. 3. IMD 10 may use any combination of electrodes to deliver therapy and/or detect electrical signals from patient 4. In some examples, therapy delivery circuitry 52 includes a charging circuit, one or more pulse generators, capacitors, transformers, switching modules, and/or other components capable of generating and/or storing energy to deliver as pacing therapy, cardiac resynchronization therapy, other therapy or a combination of therapies. In some examples, therapy delivery circuitry 52 delivers therapy as one or more electrical pulses according to one or more therapy parameter sets defining an amplitude, a frequency, a voltage or current of the therapy, or other parameters of the therapy.

Sensing circuitry 50 monitors signals from one or more combinations (also referred to as vectors) of two or more electrodes from among electrodes 14, 40, 42, 44-48, and 50 in order to monitor electrical activity of heart 6, impedance, or other electrical phenomenon. In some examples, sensing circuitry 50 includes one or more analog components, digital components or a combination thereof. In some examples, sensing circuitry 50 includes one or more sense amplifiers, comparators, filters, rectifiers, threshold detectors, analog-to-digital converters (ADCs) or the like. In some examples, sensing circuitry 50 converts sensed signals to digital form and provides the digital signals to processing circuitry 58 for processing or analysis. In one example, sensing circuitry 50 amplifies signals from electrodes 14, 40, 42, 44-48, and 50 and converts the amplified signals to multi-bit digital signals by an ADC.

In some examples, sensing circuitry 50 performs sensing of the cardiac electrogram to determine heart rates or heart rate variability, or to detect arrhythmias (e.g., tachyarrhythmias or bradycardia) or to sense other parameters or events from the cardiac electrogram. Sensing circuitry 50 may also include a switching circuitry to select which of the available electrodes (and the electrode polarity) are used to sense the heart activity, depending upon which electrode combination, or electrode vector, is used in the current sensing configuration. Processing circuitry 58 may control the switching circuitry to select the electrodes that function as sense electrodes and their polarity. Sensing circuitry 50 may include one or more detection channels, each of which may be coupled to a selected electrode configuration for detection of cardiac signals via that electrode configuration. In some examples, sensing circuitry 50 compares processed signals to a threshold to detect the existence of atrial or ventricular depolarizations and indicate the existence of the atrial depolarization (e.g., P-waves) or ventricular depolarizations (e.g., R-waves) to processing circuitry 58. Sensing circuitry 50 may comprise one or more amplifiers or other circuitry for comparison of the cardiac electrogram amplitude to a threshold, which may be adjustable.

Processing circuitry 58 may include a timing and control module, which may be embodied as hardware, firmware, software, or any combination thereof. The timing and control module may comprise a dedicated hardware circuit, such as an ASIC, separate from other processing circuitry 58 components, such as a microprocessor, or a software module executed by a component of processing circuitry 58, which may be a microprocessor or ASIC. The timing and control module may implement programmable counters. If IMD 10 is configured to generate and deliver bradycardia pacing pulses to heart 6, such counters may control the basic time intervals associated with DDD, VVI, DVI, VDD, AAI, DDI, DDDR, VVIR, DVIR, VDDR, AAIR, DDIR and other modes of pacing.

Memory 59 may be configured to store a variety of operational parameters, therapy parameters, sensed and detected data, and any other information related to the therapy and treatment of patient 4. In the example of FIG. 3, memory 59 may store sensed cardiac EGMs, e.g., associated with detected or predicted arrhythmias, and therapy parameters that define the delivery of therapy provided by therapy delivery circuitry 52. In other examples, memory 59 may act as a temporary buffer for storing data until it can be uploaded to computing system 24.

Communication circuitry 17 includes any suitable circuitry, firmware, software, or any combination thereof for communicating with another device, such as computing system 24 via network 25 of FIG. 1 or computing device 12 of FIG. 1. For example, communication circuitry 17 may include one or more antennae, modulation and demodulation circuitry, filters, amplifiers, or the like for radio frequency communication with other devices, such as computing system 24 via network 25. Under the control of processing circuitry 58, communication circuitry 17 may receive downlink telemetry from and send uplink telemetry to computing system 24 with the aid of an antenna, which may be internal and/or external. Processing circuitry 58 may provide the data to be uplinked to computing system 24 and the control signals for the telemetry circuit within communication circuitry 17, e.g., via an address/data bus. In some examples, communication circuitry 17 may provide received data to processing circuitry 58 via a multiplexer.

Power source 54 may be any type of device that is configured to hold a charge to operate the circuitry of IMD 10. Power source 54 may be provided as a rechargeable or non-rechargeable battery. In other example, power source 54 may incorporate an energy scavenging system that stores electrical energy from movement of IMD 10 within patient 4.

In accordance with the techniques of the disclosure, processing circuitry 58 senses, via sensing circuitry 50 and/or sensors 57, parametric data from patient 4. Sensors 57 may include one or more sensors, such as one or more accelerometers, pressure sensors, optical sensors for O2 saturation, etc. In some examples, the parametric data includes one or more of an activity level of the patient, a heart rate of the patient, a posture of the patient, a cardiac electrogram of the patient, a blood pressure of the patient, accelerometer data for the patient, or other types of parametric data. The activity level may, in some examples, be a summation of activity over a period of time, such as one or more seconds or minutes.

Processing circuitry 58 also determines the status of various components of IMD 10, such as the battery status (e.g., battery level, remaining battery lifetime, etc. of power source 54), impedance of leads 18, 20, and 22, as well as other information such as R-waves using the electrodes 14, 40, 42, 44-48, and 50 carried by its leads 18, 20, and 22, thresholds for therapy capture, pulse width, pacing percentage, pulse amplitude, pacing mode, pacing level changes, internal device temperature, fluid status monitored by IMD 10, and the like.

Such parametric data and device data may make up at least a portion of diagnostic data of IMD 10 determined by processing circuitry 58. Processing circuitry 58 may periodically (e.g., every minute, every hour, once a day, etc.) determine the diagnostic data of IMD 10 and communication circuitry 17 may send the determined diagnostic data to computing device 12 and/or computing system 24. In some examples, communication circuitry 17 may receive a request for diagnostic data from computing device 12 and/or computing system 24, such as via computing device 12 and/or computing system 24 interrogating IMD 10. Processing circuitry 58 may, in response to communication circuitry 17 receiving the request for diagnostic data, determine the diagnostic data of IMD 10 and may send the determined diagnostic data to computing device 12 and/or computing system 24 via communication circuitry 17.

Figure 4:
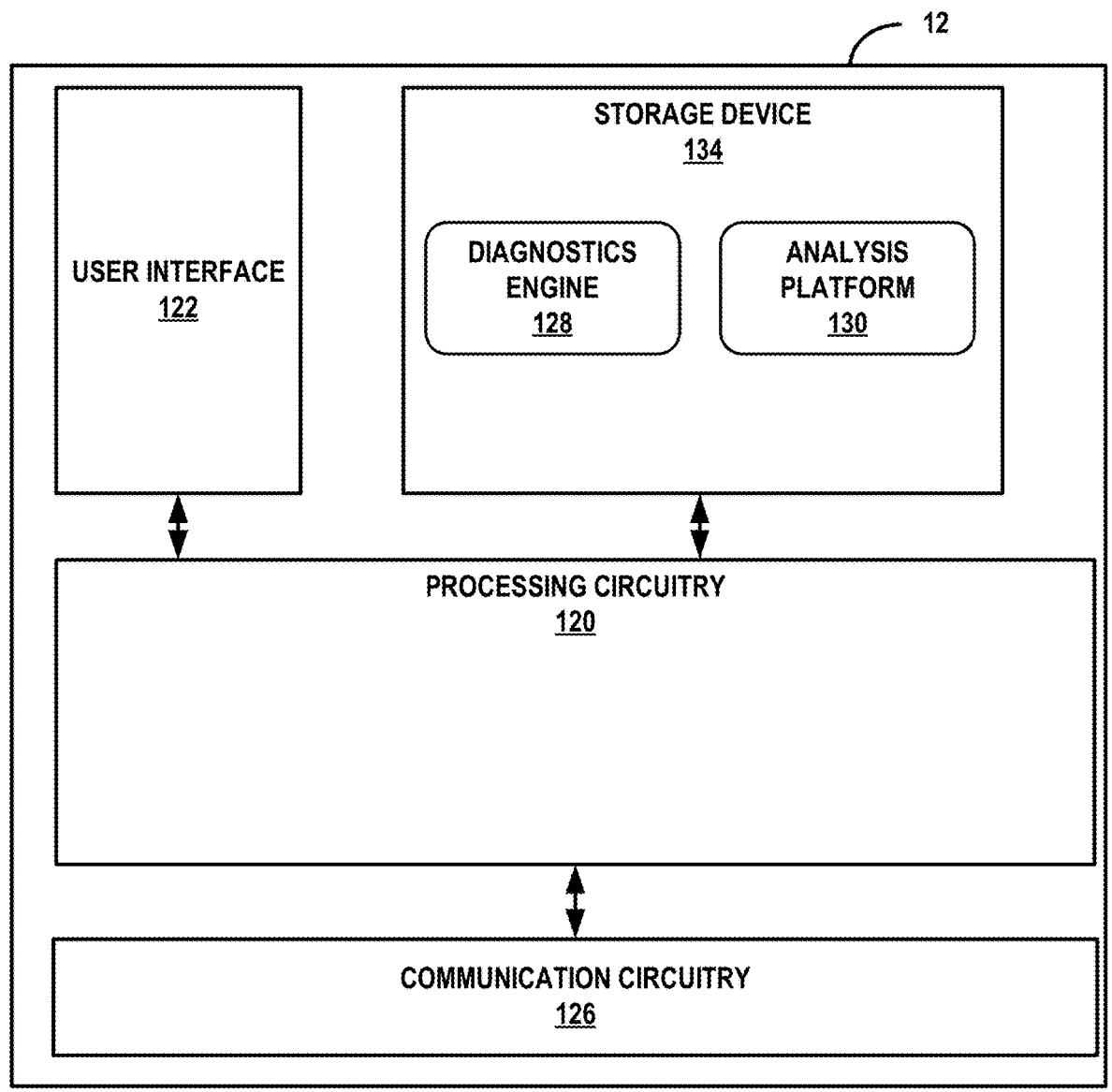
FIG. 4 is a block diagram illustrating an example configuration of a computing device.

FIG. 4 is a block diagram illustrating an example configuration of computing device 12. In the example of FIG. 4, the at least one computing device 12 includes processing circuitry 120, communication circuitry 126, storage device 134, and user interface device 122.

Processing circuitry 120 may include one or more processors that are configured to implement functionality and/or process instructions for execution within computing device 12. For example, processing circuitry 120 may be capable of processing instructions stored in storage device 134. Processing circuitry 120 may include, for example, microprocessors, a digital signal processors (DSPs), an application specific integrated circuits (ASICs), field-programmable gate arrays (FPGAs), complex programmable logic devices (CPLDs), or equivalent integrated or discrete logic circuitry, or a combination of any of the foregoing devices or circuitry. Accordingly, processing circuitry 120 may include any suitable structure, whether in hardware, software, firmware, or any combination thereof, to perform the functions ascribed herein to processing circuitry 120.

User interface device 122 includes a display (not shown), such as a liquid crystal display (LCD) or a light emitting diode (LED) display or other type of screen, with which processing circuitry 120 may present health- or device-related information, e.g., cardiac EGMs, indications of detections of impedance changes, temperature changes, etc. In addition, user interface device 122 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interface device 122 presented by processing circuitry 120 of computing device 12 and provide input.

Communication circuitry 126 may include any suitable hardware, firmware, software or any combination thereof for communicating with another device, such as IMD 10. Under the control of processing circuitry 120, communication circuitry 126 may receive downlink telemetry from, as well as send uplink telemetry to, IMD 10, or another device. Communication circuitry 126 may be configured to transmit or receive signals via inductive coupling, electromagnetic coupling, NFC, RF communication, Bluetooth®, Wi-Fi™, or other proprietary or non-proprietary wireless communication schemes. Communication circuitry 126 may also be configured to communicate with devices other than IMD 10 via any of a variety of forms of wired and/or wireless communication and/or network protocols.

Data exchanged between computing device 12, computing system 24, network 25, and IMD 10 may include operational parameters of IMD 10. Computing device 12 may transmit data, including computer-readable instructions, to IMD 10. IMD 10 may receive and implement the computer-readable instructions. In some examples, the computer-readable instructions, when implemented by IMD 10, may control IMD 10 to change one or more operational parameters, export collected data, etc. In an illustrative example, processing circuitry 120 may transmit an instruction to IMD 10 which requests IMD 10 to export collected data (e.g., sensor values, battery values, ECGs, impedance values, etc.) to computing device 12, computing system 24, and/or network 25. In turn, computing device 12, computing system 24, and/or network 25 may receive the collected data from IMD 10 and store the collected data, for example, in storage device 134. In addition, processing circuitry 120 may transmit an interrogation instruction to IMD 10 which requests IMD 10 to export operational parameters (e.g., battery, impedance, pulse width, pacing %, etc.).

In some examples, computing device 12 may be coupled to external electrodes, or to implanted electrodes via percutaneous leads. In such examples, computing device 12 may receive, from IMD 10, and monitor physiological parameters, ECGs, etc., according to one or more techniques disclosed herein.

Storage device 134 may be configured to store information within computing device 12 during operation. Storage device 134 may include a computer-readable storage medium or computer-readable storage device. In some examples, storage device 134 includes one or more of a short-term memory or a long-term memory. Storage device 134 may include, for example, read-only memory (ROM), random access memory (RAM), non-volatile RAM (NVRAM), Dynamic RAM (DRAM), Static RAM (SRAM), magnetic discs, optical discs, flash memory, forms of electrically-erasable programmable ROM (EEPROM) or erasable programmable ROM (EPROM), or any other digital media.

In some examples, storage device 134 is used to store data indicative of instructions for execution by processing circuitry 120. For example, storage device 134 may store diagnostics engine 128 that may be executed to perform techniques for interrogating IMD 10 for diagnostic data and for routing the received diagnostic data to, e.g., computing system 24. Storage device 134 may also store analysis platform 130 that may be executed by processing circuitry 120 to perform techniques for determining the operating status of IMD 10 and the health status of patient 4.

Processing circuitry 120 may execute diagnostics engine 128 to interrogate IMD 10 for diagnostic data. For example, diagnostics engine 128 may send, via communication circuitry 126, a request for diagnostic data to IMD 10 and may, in response, receive, via communication circuitry 126, the requested diagnostic data from IMD 10. Diagnostics engine 128 may, in response to receiving the requested diagnostic data from IMD 10, determine whether to route the diagnostic data to a remote computing system such as computing system 24. In some examples, computing device 12 may store a value in memory (e.g., in storage device 134) indicative of whether diagnostic data received from IMD 10 is to be analyzed on-device or analyzed remotely, and diagnostic engine 128 may look up the value in memory to determine whether to route the diagnostic data to a remote computing system such as computing system 24.

In some examples, diagnostics engine 128 may determine whether to route the diagnostic data to one or more remote computing systems, such as computing system 24, based at least in part on the use case associated with analyzing the diagnostic data out of a plurality of use cases for analyzing the diagnostic data. For example, the plurality of use cases may include next day follow-up monitoring of IMD 10, routine follow-up monitoring of IMD 10, and exception-based follow-up monitoring of IMD 10. Computing device 12 may, for example, perform on-device analysis of diagnostic data for next day follow-up monitoring of IMD 10, but may route the diagnostic data to computing system 24 to perform remote analysis of diagnostic data for routine follow-up monitoring of IMD 10 and exception-based follow-up monitoring of IMD 10.

If diagnostics engine 128 determines that diagnostic data is to be routed to one or more remote computing systems for analysis, diagnostic engine 128 may send the diagnostic data via communication circuitry 126 to one or more remote systems, such as computing system 24 via network 25. In some examples, after computing device 12 routes the diagnostic data to one or more remote systems for analysis, computing device 12 may, in response, receive the results of analyzing the diagnostic data of IMD 10 from the one or more remote systems. Computing device 12 may, in response to receiving the results of analyzing the diagnostic data, output an indication of the results at user interface device 122. For example, user interface device 122 may output an audible and/or visual indication of the operational status of IMD 10, such as an indication of whether IMD 10 is operating normally, or may present, in a user interface, the results of analyzing the diagnostic data for review by a clinician operating computing device 12.

In some examples, diagnostics engine 128 may determine that the diagnostic data received from IMD 10 is to be analyzed on-device at computing device 12. Analysis platform 130 may, in response to diagnostics engine 128 determining that the diagnostic data received from IMD 10 is to be analyzed on-device at computing device 12, execute to analyze diagnostic data to determine the operating status of IMD 10 and/or the health status of patient 4.

Analysis platform 130 may enable one or more users of computing device 12 to perform manual analysis of diagnostic data. Manual analysis of diagnostic data may be useful in an in-clinic setting where the patient is at a hospital or clinic and a user such as a doctor, a nurse, or technician is available at the hospital or clinic to perform analysis of the diagnostic data. Analysis platform 130 may output a graphical user interface at user interface device 122 with which the user may interact by providing user input at user interface device 122. The graphical user interface may present the diagnostic data so that the user may be able to view the diagnostic data and to perform one or more individual analysis on the diagnostic data. At the end of the user's analysis of the diagnostic data, analysis platform 130 may output an analysis report of the diagnostic data. For example, analysis platform 130 may print, at a printer operably coupled to computing device, a printed report of the analysis of the diagnostic data.

In some examples, analysis platform 130 may also route the diagnostic data as well as other information, such as the current use case, to a remote computing system, such as computing system 24, so that one or more users may remotely perform manual analysis of the diagnostic data. In some examples, analysis platform 130 may route diagnostic data to different remote users who have expertise in analyzing different portions of the diagnostic data. For example, analysis platform 130 may route EGM data to a certified cardiac technician (e.g., route the portion of diagnostic data that includes the EGM data of patient 4 to a remote computing device or system that is used by the certified cardiac technician) to provide a read on the arrhythmia presence in the EGM, and may route the portion or portions of the diagnostic data that includes device data (e.g., battery status, lead impedance, etc.) of IMD 10 to a trained device technician.

Analysis platform 130 may also execute to perform automatic analysis of the diagnostic data. That is, analysis platform 130 may determine the current use case for analyzing the diagnostic data, determine device characteristics data for analyzing the diagnostic data based at least in part on the current use case, and analyze the diagnostic data based at least in part on the device characteristics data to determine the operating status of IMD 10 and/or the health status of patient 4.

The current use case for analyzing the diagnostic data corresponds to the situation in which computing device 12 interrogates IMD 10 for diagnostic data. In some examples, computing device 12 may be used to interrogate IMD 10 for diagnostic data as part of next day follow-up monitoring of IMD 10 in the day after implantation of IMD 10, as part of routine follow-up monitoring of IMD 10 that may occur at regular intervals (e.g., every six months), or as part of exception-based follow-up monitoring of IMD 10 when a possible exception occurs at IMD 10. There may also be other use cases corresponding to other situations in which computing device 12 interrogates IMD 10 for diagnostic data.

Computing device 12 may, based at least in part on the current use case, determine one or more device characteristics data to be used to analyze diagnostic data received from IMD 10. Device characteristics data may be data regarding normal operations of one or more IMDs similar to IMD 10. Normal operations of the one or more IMDs may be the one or more IMDs operating to successfully achieve the intended functionalities of the one or more IMDs. The one or more IMDs similar to IMD 10 may be one or more IMDs that are the same type and model of IMDs as IMD 10 and may also be designed and manufactured by the same companies that designed and manufactured IMD 10. Computing device 12 and/or computing system 24 may collect and store a variety of different device characteristics data in memory (e.g., in storage device 134), and may select, based at least in part on the current use case, one or more of the different device characteristics data stored in memory to analyze the diagnostic data received from IMD 10. In some examples, a remote computing system, such as computing system 24, may store a collection of device characteristics data, and computing device 12 may, in response to determining the device characteristics data to be used to analyze the diagnostic data, retrieve the determined device characteristic data from the remote computing system.

The device characteristics data may include values for parameters similar to those included in the diagnostic data received from IMD 10 so that analysis platform 130 may compare the diagnostic data received from IMD 10 with the determined device characteristics data to determine the operational status of IMD 10 and/or the health status of patient 4. For example, the device characteristics data may include values for parameters such as battery status, status of therapy-delivery leads (e.g., leads 18, 20, and/or 22) such as lead impedance, sensing levels, such as a measure of R-wave amplitude, amplitude of other cardiac EGM features, signal-to-noise ratio, or another indication of the ability of IMD 10 to sense R-waves or other features of the cardiac EGM, thresholds for therapy capture, pulse width, pacing percentage, pulse amplitude, pacing mode, pacing level changes, internal device temperature, fluid status, indications of episodes of arrhythmia or other maladies, and the like.

The values for parameters included in the device characteristics data may include values for parameters over time, so that values over time for each of the parameters included in the device characteristics data may form a characteristic curve of the value for the parameter over time. Thus, for example, the device characteristics data may include a characteristics curve associated with the battery level over time (e.g., of power source 54), a characteristic curve associated with lead impedance levels over time (e.g., of leads 18, 20, and 22), a characteristic curve associated with pulse width values over time, and the like.

The device characteristics data that may be used for analyzing the received diagnostic data may include device characteristics data resulting from engineering testing, bench testing, one or more clinical trials of one or more IMDs similar to that of IMD 10, data included in one or more product manuals of IMD 10, data determined to be clinical best practices for IMD 10, data determined from performing physical modeling and/or first-principles modeling of IMD 10, accelerated aging data, validation data, pre-clinical data, and the like. For example, diagnostic data generated by one or more IMDs during such testing of the one or more IMDs may be collected and averaged to generate the device characteristics data.

The device characteristics data that may be used for analyzing the received diagnostic data may also include a history of diagnostic data previously sent by IMD 10 during operations to computing device 12 and/or computing system 24. For example, the device characteristics data may include the values for parameters included in the diagnostic data of IMD 10 that is received by computing device 12 and/or computing system 24 during the past day, the past week, the past month, and past year, and the like. Using such diagnostic data previously collected and/or determined by IMD 10 while implanted in patient 4 enables an individualized and personalized comparison and/or assessment of the operations of IMD 10 that is unique to the usage patterns of IMD 10 implanted in a unique patient 4. Computing device 12 and/or computing system 24 may receive such history of diagnostic data from IMD 10, such as a history of parameter values over time, to determine the rate of change of parameter values of IMD 10 over time, or may receive a history of programmed settings of IMD 10 relative to the history of usage patterns of IMD 10 and may use such device characteristics data that is unique to IMD 10 and patient 4 to analyze diagnostic data received from IMD 10.

The device characteristics data may also be data collected from a population of similar IMDs that are operating normally, such as from a plurality of IMDs implanted in a plurality of patients. For example, such device characteristics data may, include the average values (e.g., the mean) of each of one or more parameters over time, the maximum values of each of one or more parameters over time, the minimum values of each of one or more parameters over time, outlier values of each of one or more parameters over time, so that computing device 12 and/or computing system 24 may perform a comparison of IMD 10 against a cohort of similar IMDs. For example, for a given parameter at a particular point in time after implantation, the value for the parameter at the particular point in time may be an average of the values of the parameter at the particular point in time after implantation for the plurality of IMDs. In other examples, computing device 12 and/or computing system 24 may perform statistical comparison of diagnostic data received from IMD 10 against the data collected from a population of similar IMDs using concepts of descriptive statistics such as maximum, minimum, average, outliers, and the like to determine whether IMD 10 is operating normally. For example, computing device 12 and/or computing system 24 may determine whether the values of parameters in the diagnostic data exceeds the maximum value for the parameter in the device characteristics data, whether the values of parameters in the diagnostic data are below the minimum value for the parameter in the device characteristics data, whether any of the values of parameters in the diagnostic data is an outlier compared to the values in the device characteristics data, and the like to determine whether IMD 10 is operating normally.

To analyze the diagnostic data received from IMD 10 based at least in part on the determined device characteristics data, analysis platform 130 may select one or more parameters out of a plurality of parameters in the diagnostic data and may compare the value of each of the one or more selected parameters against the values of the corresponding one or more parameters in the device characteristics data. Thus, in some examples, analysis platform 130 may analyze every parameter specified by the diagnostic data, or may analyze a subset (i.e., fewer than all) of the parameters specified by the diagnostic data.

As described above, each parameter specified by the diagnostic data may be associated with a component of IMD 10 or may be associated with a physiological parameter of patient 4. Thus, in order to determine whether a component of IMD 10 is operating normally, analysis platform 130 may compare the value of a parameter in the diagnostic data that is associated with the component of IMD 10 with the value of a parameter in the device characteristics data that is associated with the component to determine whether the component of IMD 10 is operating normally. For example, if analysis platform 130 may determine whether the battery of IMD 10 is operating normally, analysis platform 130 may compare the value of the battery status parameter specified by the diagnostic data with the value of the battery status parameter specified by the device characteristics data to determine whether the value of the battery status parameter of IMD 10 specified by the diagnostic data indicates that the battery of IMD 10 operating normally.

In some examples, a value of a parameter associated with a component of IMD 10 as specified by the diagnostic data may indicate that the associated component of IMD 10 is operating normally if the parameter value is within a range of values associated with the value of a corresponding parameter specified by the device characteristics data. Thus, a value of a parameter associated with a component of IMD 10 as specified by the diagnostic data may indicate that the associated component of IMD 10 is operating normally even if the value does not exactly match the value of a corresponding parameter specified by the device characteristics data as long as it is within a range of values associated with the value of the corresponding parameter. For example, the range of values associated with the value of a corresponding parameter specified by the device characteristics data may be one or more standard deviations of the value of a corresponding parameter specified by the device characteristics data, a specified percentage from the value of the value of the corresponding parameter specified by the device characteristics data, and the like.

As described above, device characteristics data may include values of parameters over time, where the time may correspond to time since implantation of an IMD device. As such, device characteristics data may include, for each of one or more parameters, the parameter value over time. To compare the value of a parameter in diagnostic data with the value of a corresponding parameter in device characteristics data, analysis platform 130 may determine a time at which the diagnostic data was determined by IMD 10 in terms of the time since implantation of IMD 10 (e.g., at implantation time, one day after implantation, three months after implantation, etc.), and may determine the value of the corresponding parameter in the device characteristics data at a time that corresponds to the time at which the diagnostic data was determined by IMD 10. For example, analysis platform 130 may compare the value of the lead impedance specified by the diagnostic data determined by IMD 10 two months after implantation of IMD 10 with the value of the lead impedance at a time of two month after surgery specified by the device characteristics data.

In some examples, if the device characteristics data does not include a specific value for a parameter that corresponds to the time at which the diagnostic data was determined by IMD 10, analysis platform 130 may extrapolate a value for the parameter that corresponds to the time at which the diagnostic data was determined from the device characteristics data. For example, if the diagnostic data received from IMD 10 was determined by IMD 10 eighteen months after implantation of IMD 10, and if the device characteristics data includes values of parameters over time for up to a year after implantation of an IMD, the device characteristics data may not include values for parameters for eighteen months after implantation.

In some examples, to extrapolate a value for the parameter that corresponds to the time at which the diagnostic data was determined from the device characteristics data, analysis platform 130 may perform parametric fitting to the values for the parameter in the device characteristics data to determine a parametric survival curve. Analysis platform 130 may therefore execute to extrapolate a value for the parameter that corresponds to the time at which the diagnostic data was determined from the extrapolated parametric survival curve. In other examples, analysis platform 130 may perform any other suitable technique for extracting, from device characteristics data, values for a parameter that corresponds to a time.

The following examples illustrate the techniques described above for analyzing the diagnostic data received from IMD 10 to determine the device status of IMD 10, such as analyzing the values of one or more parameters received from IMD 10 under various use cases to determine whether components of IMD 10 associated with the one or more parameters are operating normally.

In the example where the current use case associated with analyzing the diagnostic data is next day follow-up monitoring of IMD 10, computing device 12 may determine whether components such as the battery (e.g., power source 54) and the therapy leads (e.g., leads 18, 20, and 22) of IMD 10 are operating normally in the day or days after implantation of IMD 10 in patient 4. Thus, analysis platform 130 may analyze the diagnostic data received from IMD 10 by comparing values of parameters specified by the diagnostic data that are associated with the components of IMD 10 with values of corresponding parameters of device characteristic data.

In some examples, when the current use case is next day follow-up monitoring of IMD 10, the therapy lead of IMD 10 (e.g., leads 18, 20, and 22) may be operating normally if the lead impedance and the implant-time lead impedance both fall within the range of a characterized impedance value specified by a device characteristics data and if the difference between the lead impedance and the implant-time lead impedance is no more than a specified percentage value, such as 5%.

In some examples, during surgery to implant IMD 10, computing device 12 may interrogate IMD 10 for implant-time diagnostic data and may, in response, receive the requested implant-time diagnostic data from IMD 10, which computing device 12 may store in memory (e.g., in storage devices 134) or which computing device 12 may store at a remote computing system, such as computing system 24. Thus, in response to determining that the current use case associated with analyzing the diagnostic data is next day follow-up monitoring of IMD 10, analysis platform 130 may also retrieve implant-time diagnostic data received from IMD 10. Analysis platform 130 may, in response to the current use case being next day follow-up monitoring of IMD 10, execute to use device characteristics data determined via engineering testing, bench testing, one or more clinical trials, one or more medical device product manuals, clinical best practices, first-principles modeling of the medical device, and the like.

To determine whether the therapy leads (e.g., leads 18, 20, and 22) of IMD 10 are operating normally while the current use case is next day follow-up monitoring of IMD 10, analysis platform 130 may compare the lead impedance value specify the diagnostic data associated with IMD 10 with the implant-time lead impedance value specified by the implant-time diagnostic data associated with IMD 10 to determine if the difference between the two values are within the specified percentage value, such as 5%. Analysis platform 130 may also execute to determine whether both the lead impedance value specify the diagnostic data associated and IMD 10 with the implant-time lead impedance value specified by the implant-time diagnostic data associated with IMD 10 are each within the range of a characterized impedance value specified by the determined device characteristics data.

If the device characteristics data specifies a day-after-surgery impedance value, analysis platform 130 may determine whether both the lead impedance value specify the diagnostic data associated and IMD 10 with the implant-time lead impedance value specified by the implant-time diagnostic data associated with IMD 10 are each within range of the day-after-surgery impedance value specified by the device characteristics data. For example, if the device characteristics data specifies a day-after-surgery impedance value of 750 Ohms with a range of plus-minus 114 Ohms, the lead impedance value specify the diagnostic data associated and IMD 10 with the implant-time lead impedance value specified by the implant-time diagnostic data associated with IMD 10 are each within range of the day-after-surgery impedance value if each value is within 114 Ohms of the 750 Ohms impedance value of the day-after-surgery impedance value specified by the device characteristics data.

In this way, analysis platform 130 may determine if the lead impedance value specify the diagnostic data associated and IMD 10 with the implant-time lead impedance value specified by the implant-time diagnostic data associated with IMD 10 are each within range of the day-after-surgery impedance value specified by the device characteristics data and whether the lead impedance value specify the diagnostic data associated and IMD 10 with the implant-time lead impedance value specified by the implant-time diagnostic data associated with IMD 10 differ by no more than a specified percentage. If analysis platform may determine that the lead impedance value specify the diagnostic data associated and IMD 10 with the implant-time lead impedance value specified by the implant-time diagnostic data associated with IMD 10 meet both conditions, then analysis platform 130 may determine that the therapy leads of IMD 10 (e.g., leads 18, 20, and 22) are operating normally under the use case of next day follow-up monitoring of IMD 10

In another example, when the current use case is next day follow-up monitoring of IMD 10, the therapy leads (e.g., leads 18, 20, and 22) of IMD 10 may be operating normally (i) if the lead impedance and the implant-time lead impedance both fall within the range of a characterized impedance value specified by a device characteristics data or if the lead impedance and the implant-time lead impedance both fall within the range of a corresponding impedance value for a population of IMDs operating normally, and (ii) if the difference between the lead impedance and the implant-time lead impedance is no more than a specified percentage value, such as 5%.

In this example, the analysis for determining whether the therapy leads of IMD 10 (e.g., leads 18, 20, and 22) are operating normally is similar to the example above, except that the lead impedance of IMD 10 and the implant-time lead impedance may also be compared to a corresponding lead impedance value specified by a device characteristic data determined from a population of similar IMDs that are operating normally. Thus, analysis platform 130 may, in response to determining that the current use case is next day follow-up monitoring of IMD 10, execute to use device characteristics data determined from a population of similar IMDs that are operating normally to analyze diagnostic data received from IMD 10. Analysis platform 130 may determine whether both the lead impedance value specify the diagnostic data associated and IMD 10 with the implant-time lead impedance value specified by the implant-time diagnostic data associated with IMD 10 are each within range of a corresponding day-after-surgery impedance value specified by the device characteristics data. For example, if the device characteristics data specifies a day-after-surgery impedance value of 750 Ohms with a range of plus-minus 114 Ohms, the lead impedance value specify the diagnostic data associated and IMD 10 with the implant-time lead impedance value specified by the implant-time diagnostic data associated with IMD 10 are each within range of the day-after-surgery impedance value if each value is within 114 Ohms of the 750 Ohms impedance value of the day-after-surgery impedance value specified by the device characteristics data.

Other components of IMD 10, such as the battery (e.g., power source 54) of IMD 10, may checked following similar techniques as described above with respect to the therapy leads of IMD 10 (e.g., leads 18, 20, and 22) to determine if these components are operating normally when the current use case is next day follow-up monitoring of IMD 10. Once analysis platform 130 has finished analyzing the diagnostic data of IMD 10 to determine the operating status of IMD 10, analysis platform 130 may generate an analysis report. The analysis report may indicate, for each component of IMD 10, whether computing device 12 has determined that the component is operating normally. Analysis platform 130 may output the report for display to the user at user interface device 122 and/or may upload the report to computing system 24.

In some examples, when the current use case is routine follow-up monitoring of IMD 10 or exception-based follow-up monitoring of IMD 10, computing device 12 may determine whether a component of IMD 10 is operating correct based at least in part on comparing the value of a parameter in the diagnostic data of IMD 10 associated with the component of IMD 10 with historical values of the parameter associated with the component. For example, in the case of therapy leads of IMD 10 (e.g., leads 18, 20, and 22), computing device 12 may determine whether the therapy lead is operating normally based at least in part on comparing the lead impedance value specified by the diagnostic data with historical lead impedance values of the therapy lead.

In some examples, when the current use case is routine follow-up monitoring of IMD 10 or exception-based follow-up monitoring of IMD 10, computing device 12 may determine that the therapy lead of IMD 10 is operating normally if the lead impedance falls within the range of a characterized value specified by a device characteristics data, if the lead impedance is between the historical maximum and minimum lead impedance values for IMD 10, and if the lead impedance is within a specified percentage, such as 10%, of the average impedance value for IMD 10 over the previous two weeks.

In this case, analysis platform 130 may analyze the lead impedance value specified by the diagnostic data based on both the device characteristics data determined via engineering testing, bench testing, or one or more clinical trials, device characteristics data in one or more medical device product manuals, device characteristics data associated with clinical best practices, device characteristics data determined from first-principles modeling of the medical device, as well as the device characteristics data that contains the history of diagnostic data previously sent by IMD 10 during operations to computing device 12. The device characteristics data that contains the history of diagnostic data previously sent by IMD 10 during operations may be a collection of diagnostic data that are regularly sent (e.g., once a day) from IMD 10 to computing device 12.

To determine whether the lead impedance falls within the range of a characterized value specified by a device characteristics data, analysis platform 130 may determine the time at which the diagnostic data received by computing device 12 was determined by IMD 10, where the time is the time after implantation of IMD 10, such as in terms of number of days, weeks, months, and the like. Analysis platform 130 may determine an impedance value specified by the device characteristics data determined via engineering testing, bench testing, or one or more clinical trials that corresponds to the time at which the diagnostic data received by computing device 12 was determined by IMD 10, and compare the lead impedance value specified by the diagnostic data for IMD 10 with the impedance value specified by the device characteristics data that corresponds to the time. Thus, for example, if the time which the diagnostic data received by computing device 12 was determined by IMD 10 is ten weeks after implantation of IMD 10, the impedance value specified by the device characteristics data that corresponds to the time may be the impedance value in the device characteristics data that corresponds to ten weeks after implantation of an IMD.

For example, if the lead impedance value specified by the diagnostic data for IMD 10 is 600 Ohms, analysis platform 130 may determine whether the lead impedance value specified by the diagnostic data for IMD 10 is within plus-minus 85 Ohms of the impedance value specified by the device characteristics data and, if so, may determine that the lead impedance value specified by the diagnostic data for IMD 10 is within range of the impedance value specified by the device characteristics data.

In some examples, the time at which the diagnostic data received by computing device 12 was determined by IMD 10, where the time is the time after implantation of IMD 10 may extend beyond the time range associated with the values in the device characteristics data determined via engineering testing, bench testing, one or more clinical trials, one or more medical device product manuals, clinical best practices, or first-principles modeling of the medical device. For example, if the device characteristics data contains values for up to twelve weeks after implantation of the IMD, and if the diagnostic data was determined by IMD at fourteen weeks after implantation of IMD 10, the device characteristics data may not include values that corresponds to fourteen weeks after implantation.

In this case, analysis platform 130 may, in response to determining that the time at which IMD 10 determines the diagnostic data is beyond the time range associated with the device characteristics data, execute to extrapolate values for times beyond the time range associated with the device characteristics data from the values specified by the device characteristics data. For example, analysis platform 130 may perform parametric fitting to determine a parametric survival curve based on the values specified by the device characteristics data and may, based on the parametric survival curve, extrapolate one or more values for the device characteristic data that corresponds to the time at which IMD 10 determines the diagnostic data. For example, if the device characteristics data specifies twelve weeks of impedance values, analysis platform 130 may perform parametric fitting based on the twelve weeks of impedance values to determine a parametric survival curve of impedance values, and may extract an impedance value for fourteen weeks after implantation of an IMD based on the parametric survival curve. Analysis platform 130 may therefore compare the lead impedance value specified by the diagnostic data for IMD 10 with the extracted impedance value to determine whether the therapy lead of IMD 10 is operating normally.

To determine whether the lead impedance between the historical maximum and minimum lead impedance values for IMD 10, analysis platform 130 may determine, from device characteristics data that contains the history of diagnostic data previously sent by IMD 10 during operations to computing device 12, the historical maximum and minimum lead impedance values for IMD 10, and may determine whether the lead impedance between the historical maximum and minimum lead impedance values for IMD 10. Similarly, to determine whether the lead impedance is within a specified percentage, such as 10%, of the average impedance value for IMD 10 over the previous two weeks, analysis platform 130 may determine, from device characteristics data that contains the history of diagnostic data previously sent by IMD 10 during operations to computing device 12, the average impedance value for IMD 10 over the previous two weeks, and may determine whether the lead impedance is within the specified percentage of the determined average impedance value for IMD 10.

In another example, when the current use case is routine follow-up monitoring of IMD 10 or exception-based follow-up monitoring of IMD 10, computing device 12 may compare values of parameters specified by the diagnostic data received from IMD 10 against values specified by a device characteristic data determined from collecting diagnostic data determined by a population of similar IMDs that are operating normally in the field as an alternative to the device characteristics data determined via engineering testing, bench testing, or one or more clinical trials. Using such device characteristic data determined from collecting diagnostic data determined by a population of similar IMDs that are operating normally in the field may provide some potential advantages compared with device characteristics data determined via engineering testing, bench testing, or one or more clinical trials. For example, the device characteristics data determined from collecting diagnostic data determined by a population of similar IMDs may include data over an extended duration of time compared with the data that may be available from bench testing or clinical trials, therefore potentially obviating having to extrapolate data, as described above. Further, the device characteristics data determined from collecting diagnostic data determined by a population of similar IMDs may be real data in the sense that they are data of IMDs operating in patients in the field versus simulated data that is determined via from bench testing or clinical trials.

Thus, in some examples, when the current use case is routine follow-up monitoring of IMD 10 or exception-based follow-up monitoring of IMD 10, computing device 12 may determine that the therapy lead of IMD 10 is operating normally if the lead impedance falls within the range of a characterized value specified by a device characteristics data or if the lead impedance falls within the range of values for normal operations of a population of similar IMDs, if the lead impedance is between the historical maximum and minimum lead impedance values for IMD 10, and if the lead impedance is within a specified percentage, such as 10%, of the average impedance value for IMD 10 over the previous two weeks.

To determine whether the lead impedance falls within the range of values for normal operations of a population of similar IMDs, analysis platform 130 may analyze the lead impedance value specified by the diagnostic data based on the device characteristics data determined from collecting diagnostic data determined by a population of similar IMDs. The device characteristics data may specify, for a particular time after implantation, an impedance value that is the average of the impedance values for the particular time after implantation from the population of similar IMDs. Analysis platform 130 may therefore compare the lead impedance value specified by the diagnostic data for a particular time after implementation with the impedance value specified by the device characteristics data for the particular time to determine whether the therapy lead for IMD 10 is operating normally.

Other components of IMD 10, such as the battery (e.g., power source 54) of IMD 10, may checked following similar techniques as described above with respect to the therapy lead of IMD 10 to determine if these components are operating normally when the current use case is routine follow-up monitoring of IMD 10 or exception-based follow-up monitoring of IMD 10. Once analysis platform 130 has finished analyzing the diagnostic data of IMD 10 to determine the operating status of IMD 10, analysis platform 130 may generate an analysis report. The analysis report may indicate, for each component of IMD 10, whether computing device 12 has determined that the component is operating normally. Analysis platform 130 may output the report for display to the user at user interface device 122 and/or may upload the report to computing system 24.

Figure 5:
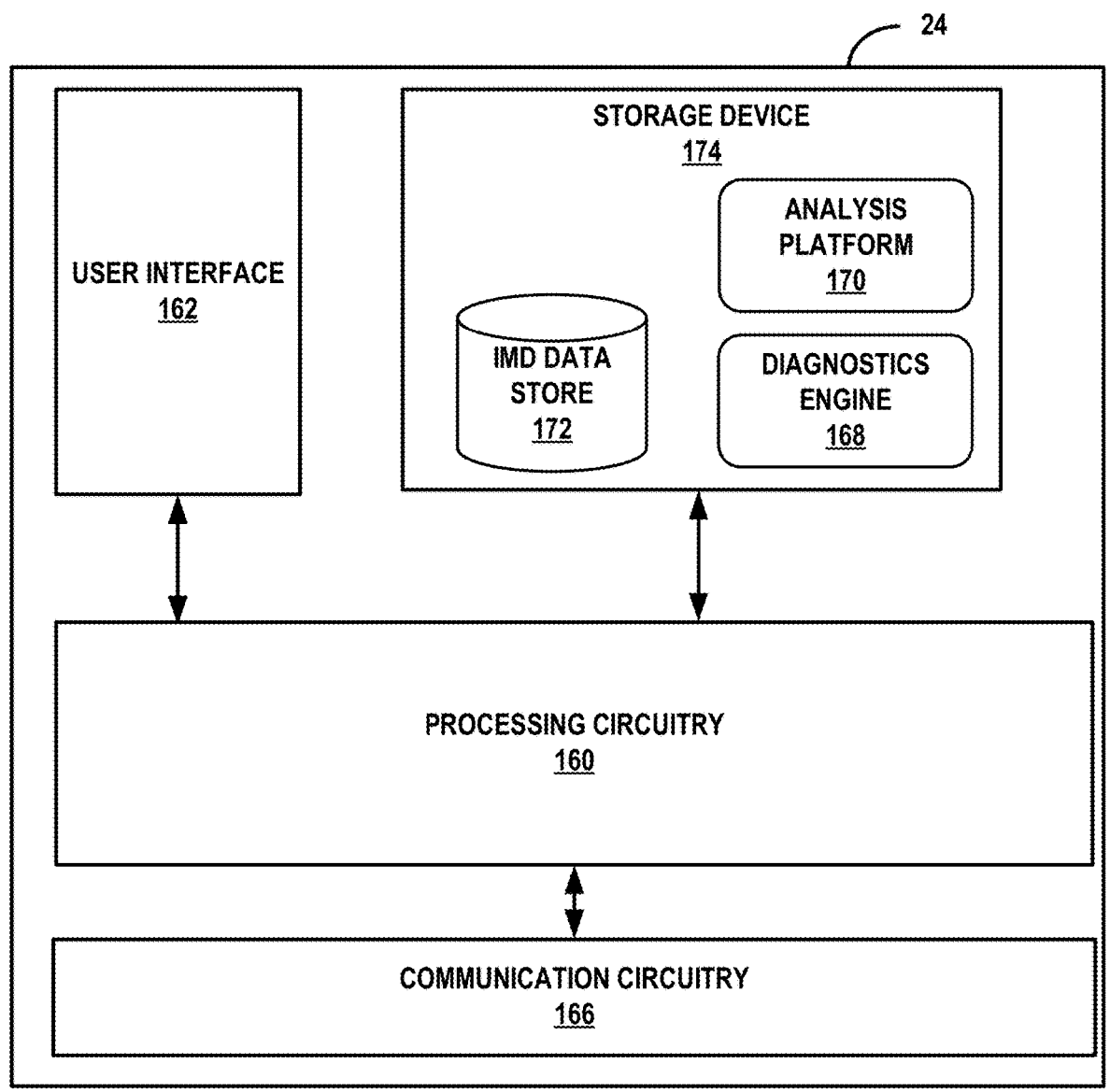
FIG. 5 is a block diagram illustrating an example configuration of a computing system.

FIG. 5 is a block diagram illustrating an example configuration of computing system 24. In the example of FIG. 5, the at least one computing device 12 includes processing circuitry 160, communication circuitry 166, storage device 174, and user interface device 162. Computing system 24 may be any component or system that includes processing circuitry or other suitable computing environment for executing software instructions and, for example, need not necessarily include one or more elements shown in FIG. 5 (e.g., communication circuitry 166, storage device 174, and user interface device 162; and in some examples components such as storage device 174 may not be co-located or in the same chassis as other components). In some examples, computing system 24 may be a cloud computing system distributed across a plurality of devices.

Processing circuitry 160 may include one or more processors that are configured to implement functionality and/or process instructions for execution within computing system 24. For example, processing circuitry 160 may be capable of processing instructions stored in storage device 174. Processing circuitry 160 may include, for example, microprocessors, a digital signal processors (DSPs), an application specific integrated circuits (ASICs), field-programmable gate arrays (FPGAs), complex programmable logic devices (CPLDs), or equivalent integrated or discrete logic circuitry, or a combination of any of the foregoing devices or circuitry. Accordingly, processing circuitry 160 may include any suitable structure, whether in hardware, software, firmware, or any combination thereof, to perform the functions ascribed herein to processing circuitry 160.

User interface device 162 includes a display (not shown), such as a liquid crystal display (LCD) or a light emitting diode (LED) display or other type of screen, with which processing circuitry 160 may present health- or device-related information, e.g., cardiac EGMs, indications of detections of impedance changes, temperature changes, etc. In addition, user interface device 162 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interface device 162 presented by processing circuitry 160 of computing device 12 and provide input.

Communication circuitry 166 may include any suitable hardware, firmware, software or any combination thereof for communicating with another device, such as computing device 12 and/or IMD 10, via network 25. For example, communication circuitry 166 may include a network interface card, such as an Ethernet card, an optical transceiver, a radio frequency transceiver, or any other type of device that can send and receive information. Under the control of processing circuitry 160, communication circuitry 166 may receive downlink telemetry from, as well as send uplink telemetry to, IMD 10, or another device. Communication circuitry 166 may be configured to transmit or receive signals via RF communication, Bluetooth®, Wi-Fi™ or other any of a variety of forms of wired and/or wireless communication and/or network protocols.

Storage device 174 may be configured to store information within computing device 12 during operation. Storage device 174 may include a computer-readable storage medium or computer-readable storage device. In some examples, storage device 174 includes one or more of a short-term memory or a long-term memory. Storage device 174 may include, for example, read-only memory (ROM), random access memory (RAM), non-volatile RAM (NVRAM), Dynamic RAM (DRAM), Static RAM (SRAM), magnetic discs, optical discs, flash memory, forms of electrically-erasable programmable ROM (EEPROM) or erasable programmable ROM (EPROM), or any other digital media.

In some examples, storage device 174 is used to store data indicative of instructions for execution by processing circuitry 160. For example, storage device 174 may store diagnostics engine 168 that may be executed to perform techniques for interrogating IMD 10 for diagnostic data and for routing the received diagnostic data to, e.g., computing system 24. Storage device 174 may also store analysis platform 170 that may be executed by processing circuitry 160 to perform techniques for determining the operating status of IMD 10 and the health status of patient 4.

In accordance with the techniques of this disclosure, computing system 24 may receive diagnostic data that IMD 10 may create in response to being interrogated by computing device 12. Computing system 24 may store such diagnostic data and may also analyze the diagnostic data to determine the operating status of IMD 10. In some examples, computing system 24 may provide an analysis platform that enables users to perform manual analysis of the diagnostic data to determine the operating status of IMD 10 and/or the health status of patient 4.

Processing circuitry 160 may execute diagnostics engine 168 to receive, from computing device 12 and/or IMD 10, diagnostic data created by IMD 10 as a result of computing device 12 interrogating IMD 10 for the diagnostic data and to store the diagnostic data in IMD data store 172. Because IMD 10 may periodically create diagnostic data that is then sent to computing device 12, computing system 24 may store a history of diagnostic data created by IMD 10 in IMD data store 172.

Diagnostics engine 168 may determine that the diagnostic data created by IMD 10 and received from computing device 12 and/or IMD 10 is to be analyzed at computing system 24. In some examples, if diagnostic engine 168 has already analyzed the diagnostic data, computing system 24 may not also analyze the diagnostic data. Instead, computing system 24 may receive the result of the analysis performed by computing device 12, such as a report that indicates whether IMD 10 is operating normally and/or that indicates the health of patient 4, and may store the results of such analysis in IMD data store 172.

Processing circuitry 160 may execute analysis platform to analyze the diagnostic data received by computing system 24. Analysis platform 170 may, in response to diagnostics engine 168 determining that the diagnostic data is to be analyzed by computing system 24, analyze diagnostic data to determine the operating status of IMD 10 and/or the health status of patient 4.

Analysis platform 170 may enable one or more users of computing device 12 to perform manual analysis of diagnostic data. Analysis platform 170 may also perform automatic analysis of the diagnostic data, similar to the techniques described with respect to computing system 24 in FIG. 4. That is, analysis platform 170 may determine the current use case for analyzing the diagnostic data, determine device characteristics data for analyzing the diagnostic data based at least in part on the current use case, and analyze the diagnostic data based at least in part on the device characteristics data to determine the operating status of IMD 10 and/or the health status of patient 4.

Computing system 24 may, based at least in part on the current use case, determine one or more device characteristics data to be used to analyze diagnostic data received from IMD 10. Computing system 24 and/or computing system 24 may collect and store a variety of different device characteristics data in memory (e.g., in IMD data store 172 of storage device 174), and analysis platform 170 may select, based at least in part on the current use case, one or more of the different device characteristics data stored in memory to analyze the diagnostic data received from IMD 10.

To analyze the diagnostic data created by IMD 10 based at least in part on the determined device characteristics data, analysis platform 170 may select one or more parameters out of a plurality of parameters in the diagnostic data and may compare the parameter values of each of the one or more selected parameters against the parameter values of the corresponding one or more parameters in the device characteristics data. Thus, in some examples, analysis platform 170 may analyze the values of every parameter specified by the diagnostic data, or may analyze the values of a subset (i.e., fewer than all) of the parameters specified by the diagnostic data.

As described above, each parameter value specified by the diagnostic data may be associated with a component of IMD 10 or may be associated with a physiological parameter of patient 4. Thus, in order to determine whether a component of IMD 10 is operating normally, analysis platform 170 may compare the parameter value in the diagnostic data that is associated with the component of IMD 10 with the parameter value in the device characteristics data that is associated with the component to determine whether the component of IMD 10 is operating normally. For example, if analysis platform 170 may determine whether the battery (e.g., power source 54) of IMD 10 is operating normally, analysis platform 170 may compare the battery status value (e.g., the battery discharge level) specified by the diagnostic data with the battery status value parameter specified by the device characteristics data to determine whether the battery status value specified by the diagnostic data indicates that the battery of IMD 10 operating normally.

In some examples, a parameter value associated with a component of IMD 10 as specified by the diagnostic data may indicate that the associated component of IMD 10 is operating normally if the parameter value is within a range of values associated with the value of a corresponding parameter specified by the device characteristics data. Thus, a value of a parameter associated with a component of IMD 10 as specified by the diagnostic data may indicate that the associated component of IMD 10 is operating normally even if the value does not exactly match the value of a corresponding parameter specified by the device characteristics data as long as it is within a range of values associated with the value of the corresponding parameter. For example, the range of values associated with the value of a corresponding parameter specified by the device characteristics data may be one or more standard deviations of the value of a corresponding parameter specified by the device characteristics data, a specified percentage from the value of the value of the corresponding parameter specified by the device characteristics data, and the like.

As described above, device characteristics data may include values of parameters over time, where the time may correspond to time since implantation of an IMD device. As such, device characteristics data may include, for each of one or more parameters, the parameter value over time. To compare the value of a parameter in diagnostic data with the value of a corresponding parameter in device characteristics data, analysis platform 170 may determine a time at which the diagnostic data was determined by IMD 10 in terms of the time since implantation of IMD 10 (e.g., at implantation time, one day after implantation, three months after implantation, etc.), and may determine the value of the corresponding parameter in the device characteristics data at a time that corresponds to the time at which the diagnostic data was determined by IMD 10. For example, analysis platform 170 may compare the value of the lead impedance specified by the diagnostic data determined by IMD 10 two months after implantation of IMD 10 with the value of the lead impedance at a time of two month after surgery specified by the device characteristics data.

In some examples, if the device characteristics data does not include a specific value for a parameter that corresponds to the time at which the diagnostic data was determined by IMD 10, analysis platform 170 may extrapolate a value for the parameter that corresponds to the time at which the diagnostic data was determined from the device characteristics data. For example, if the diagnostic data received from IMD 10 was determined by IMD 10 eighteen months after implantation of IMD 10, and if the device characteristics data includes values of parameters over time for up to a year after implantation of an ID, the device characteristics data may not include values for parameters for eighteen months after implantation.

In some examples, to extrapolate a value for the parameter that corresponds to the time at which the diagnostic data was determined from the device characteristics data, analysis platform 170 may perform parametric fitting to the values for the parameter in the device characteristics data to determine a parametric survival curve. Analysis platform 170 may therefore execute to extrapolate a value for the parameter that corresponds to the time at which the diagnostic data was determined from the extrapolated parametric survival curve. In other examples, analysis platform 170 may perform any other suitable technique for extracting, from device characteristics data, values for a parameter that corresponds to a time.

The following examples illustrate the techniques described above for analyzing the diagnostic data received from IMD 10 to determine the device status of IMD 10, such as analyzing the values of one or more parameters received from IMD 10 under various use cases to determine whether components of IMD 10 associated with the one or more parameters are operating normally.

In the example where the current use case associated with analyzing the diagnostic data is next day follow-up monitoring of IMD 10, computing system 24 may determine whether components such as the battery (e.g., power source 54) and the therapy leads (e.g., leads 18, 20, and 22) of IMD 10 are operating normally in the day or days after implantation of IMD 10 in patient 4. Thus, analysis platform 170 may analyze the diagnostic data received from IMD 10 by comparing values of parameters specified by the diagnostic data that are associated with the components of IMD 10 with values of corresponding parameters of device characteristic data.

In some examples, when the current use case is next day follow-up monitoring of IMD 10, the therapy lead of IMD 10 may be operating normally if the lead impedance and the implant-time lead impedance both fall within the range of a characterized impedance value specified by a device characteristics data and if the difference between the lead impedance and the implant-time lead impedance is no more than a specified percentage value, such as 5%.

In some examples, during surgery to implant IMD 10, computing system 24 may interrogate IMD 10 for implant-time diagnostic data and may, in response, receive the requested implant-time diagnostic data from IMD 10, which computing system 24 may store in memory (e.g., in IMD data store 172 of storage devices 174). Thus, in response to determining that the current use case associated with analyzing the diagnostic data is next day follow-up monitoring of IMD 10, analysis platform 170 may also retrieve implant-time diagnostic data received from IMD 10. Analysis platform 170 may, in response to the current use case being next day follow-up monitoring of IMD 10, execute to use device characteristics data determined via engineering testing, bench testing, one or more clinical trials, one or more medical device product manuals, clinical best practices, or first-principles modeling of the medical device.

To determine whether the therapy lead of IMD 10 is operating normally while the current use case is next day follow-up monitoring of IMD 10, analysis platform 170 may compare the lead impedance value of IMD 10 specified in the diagnostic data with the implant-time lead impedance value of IMD 10 specified by the implant-time diagnostic data to determine if the difference between the two values are within the specified percentage value, such as 5%.

Analysis platform 170 may also execute to determine whether the lead impedance value of IMD 10 specified in the diagnostic data and the implant-time lead impedance value of IMD 10 specified by the implant-time diagnostic data are each within the range of a characterized impedance value specified by the determined device characteristics data.

If the device characteristics data specifies a day-after-surgery impedance value, analysis platform 170 may determine whether both the lead impedance value of IMD 10 specified in the diagnostic data and the implant-time lead impedance value of IMD 10 specified by the implant-time diagnostic data are each within range of the day-after-surgery impedance value specified by the device characteristics data. For example, if the device characteristics data specifies a day-after-surgery impedance value of 750 Ohms with a range of plus-minus 114 Ohms, the lead impedance value of IMD 10 specified in the diagnostic data and the implant-time lead impedance value of IMD 10 specified by the implant-time diagnostic data are each within range of the day-after-surgery impedance value if each value is within 114 Ohms of the 750 Ohms impedance value of the day-after-surgery impedance value specified by the device characteristics data.

In this way, analysis platform 170 may determine if the lead impedance value of IMD 10 specified in the diagnostic data and the implant-time lead impedance value of IMD 10 specified by the implant-time diagnostic data are each within range of the day-after-surgery impedance value specified by the device characteristics data and whether the lead impedance value of IMD 10 specified in the diagnostic data and the implant-time lead impedance value of IMD 10 specified by the implant-time diagnostic data differ by no more than a specified percentage. If analysis platform may determine that the lead impedance value of IMD 10 specified in the diagnostic data and the implant-time lead impedance value of IMD 10 specified by the implant-time diagnostic data meet both conditions, then analysis platform 170 may determine that the therapy lead of IMD 10 is operating normally under the use case of next day follow-up monitoring of IMD 10

In another example, when the current use case is next day follow-up monitoring of IMD 10, the therapy lead of IMD 10 (e.g., leads 18, 20, and 22) may be operating normally (i) if the lead impedance and the implant-time lead impedance both fall within the range of a characterized impedance value specified by a device characteristics data or if the lead impedance and the implant-time lead impedance both fall within the range of a corresponding impedance value for a population of IMDs operating normally, and (ii) if the difference between the lead impedance and the implant-time lead impedance is no more than a specified percentage value, such as 5%.

In this example, the analysis for determining whether the therapy lead of IMD 10 is operating normally is similar to the example above, except that the lead impedance of IMD 10 and the implant-time lead impedance may also be compared to a corresponding lead impedance value specified by a device characteristic data determined from a population of similar IMDs that are operating normally. Thus, analysis platform 170 may, in response to determining that the current use case is next day follow-up monitoring of IMD 10, execute to use device characteristics data determined from a population of similar IMDs that are operating normally to analyze diagnostic data received from IMD 10. Analysis platform 170 may determine whether both the lead impedance value of IMD 10 specified in the diagnostic data and the implant-time lead impedance value of IMD 10 specified by the implant-time diagnostic data are each within range of a corresponding day-after-surgery impedance value specified by the device characteristics data. For example, if the device characteristics data specifies a day-after-surgery impedance value of 750 Ohms with a range of plus-minus 114 Ohms, the lead impedance value of IMD 10 specified in the diagnostic data and the implant-time lead impedance value of IMD 10 specified by the implant-time diagnostic data are each within range of the day-after-surgery impedance value if each value is within 114 Ohms of the 750 Ohms impedance value of the day-after-surgery impedance value specified by the device characteristics data.

Other components of IMD 10, such as the battery of IMD 10 (e.g., power source 54), may be analyzed using similar techniques as described above with respect to the therapy leads (e.g., leads 18, 20, and 22) of IMD 10 to determine if these components are operating normally when the current use case is next day follow-up monitoring of IMD 10. Once analysis platform 170 has finished analyzing the diagnostic data of IMD 10 to determine the operating status of IMD 10, analysis platform 170 may generate an analysis report. The analysis report may indicate, for each component of IMD 10, whether computing system 24 has determined that the component is operating normally. Analysis platform 170 may output the report for display to the user at user interface device 162 and/or may upload the report to computing system 24.

In some examples, when the current use case is routine follow-up monitoring of IMD 10 or exception-based follow-up monitoring of IMD 10, computing system 24 may determine whether a component of IMD 10 is operating correct based at least in part on comparing the value of a parameter in the diagnostic data of IMD 10 associated with the component of IMD 10 with historical values of the parameter associated with the component. For example, in the case of a therapy lead of IMD 10, computing system 24 may determine whether the therapy lead is operating normally based at least in part on comparing the lead impedance value specified by the diagnostic data with historical lead impedance values of the therapy lead.

In some examples, when the current use case is routine follow-up monitoring of IMD 10 or exception-based follow-up monitoring of IMD 10, computing system 24 may determine that the therapy lead of IMD 10 is operating normally if the lead impedance falls within the range of a characterized value specified by a device characteristics data, if the lead impedance is between the historical maximum and minimum lead impedance values for IMD 10, and if the lead impedance is within a specified percentage, such as 10%, of the average impedance value for IMD 10 over the previous two weeks.

In this case, analysis platform 170 may analyze the lead impedance value specified by the diagnostic data based on both the device characteristics data determined via engineering testing, bench testing, or one or more clinical trials as well as the device characteristics data that contains the history of diagnostic data previously sent by IMD 10 during operations to computing system 24. The device characteristics data that contains the history of diagnostic data previously sent by IMD 10 during operations may be a collection of diagnostic data that are regularly sent (e.g., once a day) from IMD 10 to computing system 24.

To determine whether the lead impedance falls within the range of a characterized value specified by a device characteristics data, analysis platform 170 may determine the time at which the diagnostic data received by computing system 24 was determined by IMD 10, where the time is the time after implantation of IMD 10, such as in terms of number of days, weeks, months, and the like. Analysis platform 170 may determine an impedance value specified by the device characteristics data determined via engineering testing, bench testing, or one or more clinical trials that corresponds to the time at which the diagnostic data received by computing system 24 was determined by IMD 10, and compare the lead impedance value specified by the diagnostic data with the impedance value specified by the device characteristics data that corresponds to the time. Thus, for example, if the time which the diagnostic data received by computing system 24 was determined by IMD 10 is ten weeks after implantation of IMD 10, the impedance value specified by the device characteristics data that corresponds to the time may be the impedance value in the device characteristics data that corresponds to ten weeks after implantation of an IMD.

For example, if the lead impedance value specified by the diagnostic data for IMD 10 is 1600 Ohms, analysis platform 170 may determine whether the lead impedance value specified by the diagnostic data for IMD 10 is within plus-minus 85 Ohms of the impedance value specified by the device characteristics data and, if so, may determine that the lead impedance value specified by the diagnostic data for IMD 10 is within range of the impedance value specified by the device characteristics data.

In some examples, the time at which the diagnostic data received by computing system 24 was determined by IMD 10, where the time is the time after implantation of IMD 10, may extend beyond the time range associated with the values in the device characteristics data determined via engineering testing, bench testing, or one or more clinical trials. For example, if the device characteristics data contains values for up to twelve weeks after implantation of the IMD, and if the diagnostic data was determined by IMD at fourteen weeks after implantation of IMD 10, the device characteristics data may not include values that corresponds to fourteen weeks after implantation.

In this case, analysis platform 170 may, in response to determining that the time at which IMD 10 determines the diagnostic data is beyond the time range associated with the device characteristics data, execute to extrapolate values for times beyond the time range associated with the device characteristics data from the values specified by the device characteristics data. For example, analysis platform 170 may perform parametric fitting to determine a parametric survival curve based on the values specified by the device characteristics data and may, based on the parametric survival curve, extrapolate one or more values for the device characteristic data that corresponds to the time at which IMD 10 determines the diagnostic data. For example, if the device characteristics data specifies twelve weeks of impedance values, analysis platform 170 may perform parametric fitting based on the twelve weeks of impedance values to determine a parametric survival curve of impedance values, and may extract an impedance value for fourteen weeks after implantation of an IMD based on the parametric survival curve. Analysis platform 170 may therefore compare the lead impedance value specified by the diagnostic data for IMD 10 with the extracted impedance value to determine whether the therapy lead of IMD 10 is operating normally.

To determine whether the lead impedance is between the historical maximum and minimum lead impedance values for IMD 10, analysis platform 170 may determine, from device characteristics data that contains the history of diagnostic data previously sent by IMD 10 during operations to computing system 24, the historical maximum and minimum lead impedance values for IMD 10, and may determine whether the lead impedance is between the historical maximum and minimum lead impedance values for IMD 10. Similarly, to determine whether the lead impedance is within a specified percentage, such as 10%, of the average impedance value for IMD 10 over the previous two weeks, analysis platform 170 may determine, from device characteristics data that contains the history of diagnostic data previously sent by IMD 10 during operations to computing system 24, the average impedance value for IMD 10 over the previous two weeks, and may determine whether the lead impedance is within the specified percentage of the determined average impedance value for IMD 10.

In another example, when the current use case is routine follow-up monitoring of IMD 10 or exception-based follow-up monitoring of IMD 10, computing system 24 may compare values of parameters specified by the diagnostic data received from IMD 10 against values specified by a device characteristic data determined from collecting diagnostic data determined by a population of similar IMDs that are operating normally in the field as an alternative to the device characteristics data determined via engineering testing, bench testing, or one or more clinical trials.

Thus, in some examples, when the current use case is routine follow-up monitoring of IMD 10 or exception-based follow-up monitoring of IMD 10, computing system 24 may determine that the therapy lead of IMD 10 is operating normally if the lead impedance falls within the range of a characterized value specified by a device characteristics data or if the lead impedance falls within the range of values for normal operations of a population of similar IMDs, if the lead impedance is between the historical maximum and minimum lead impedance values for IMD 10, and if the lead impedance is within a specified percentage, such as 10%, of the average impedance value for IMD 10 over the previous two weeks.

To determine whether the lead impedance falls within the range of values for normal operations of a population of similar IMDs, analysis platform 170 may analyze the lead impedance value specified by the diagnostic data based on the device characteristics data determined from collecting diagnostic data determined by a population of similar IMDs. The device characteristics data may specify, for a particular time after implantation, an impedance value that is the average of the impedance values for the particular time after implantation from the population of similar IMDs. Analysis platform 170 may therefore compare the lead impedance value specified by the diagnostic data for a particular time after implementation with the impedance value specified by the device characteristics data for the particular time to determine whether the therapy lead for IMD 10 is operating normally.

Other components of IMD 10, such as the battery of IMD 10, may checked following similar techniques as described above with respect to the therapy lead of IMD 10 to determine if these components are operating normally when the current use case is routine follow-up monitoring of IMD 10 or exception-based follow-up monitoring of IMD 10. Once analysis platform 170 has finished analyzing the diagnostic data of IMD 10 to determine the operating status of IMD 10, analysis platform 170 may generate an analysis report. The analysis report may indicate, for each component of IMD 10, whether computing system 24 has determined that the component is operating normally. Analysis platform 170 may output the report for display to the user at user interface device 162 and/or may store the report in IMD data store 172.

Figure 6:
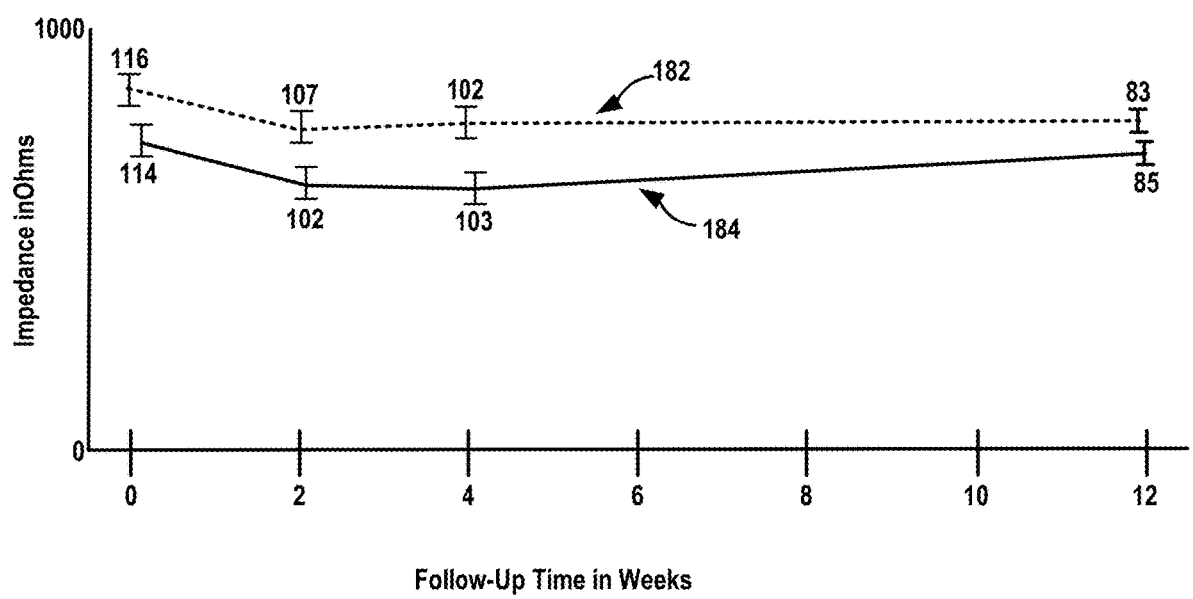
FIG. 6 is a graph of example impedance values of a ventricular lead of an example IMD characterized with clinical trials.

FIG. 6 is a graph of example impedance values of a ventricular lead of an example IMD characterized with clinical trials. Such values characterized with clinical trials may make up the device characteristics data against which the diagnostic data of an IMD, such as IMD 10, may be compared to determine the operating status of the IMD. As shown in FIG. 6 characteristic curve 182 and characteristic curve 184 are characteristic curves of example impedance values for two different models of ventricular leads, such as leads 18, 20, and 22 of IMD 10.

During clinical trials for a model of a ventricular lead, one or more ventricular leads of the same model are tested to determine the impedance values of the different ventricular leads over time, and the different impedance values are averaged (e.g., by taking the mean) to create characteristic curves such as characteristic curves 182 and 184, which plots the mean impedance value determined from the clinical trials over time. Thus, when a lead impedance value specified by a diagnostic data of IMD 10 is compared against device characteristic data determined from clinical trials, the lead impedance value specified by a diagnostic data of IMD 10 may be compared against a mean impedance value.

The values of characteristic curves 182 and 184 may each have an associated range that is based on the standard error of the mean impedance values of characteristic curves 182 and 184. As described above with respect to FIGS. 4 and 5, when a value specified by the diagnostic data of IMD 10 is compared with a corresponding value in a device characteristics data, the value specified by the diagnostic data may match the corresponding value in the device characteristics data if the value specified by the diagnostic data is within a range of values associated with the corresponding value in the device characteristics data.

Figure 7:
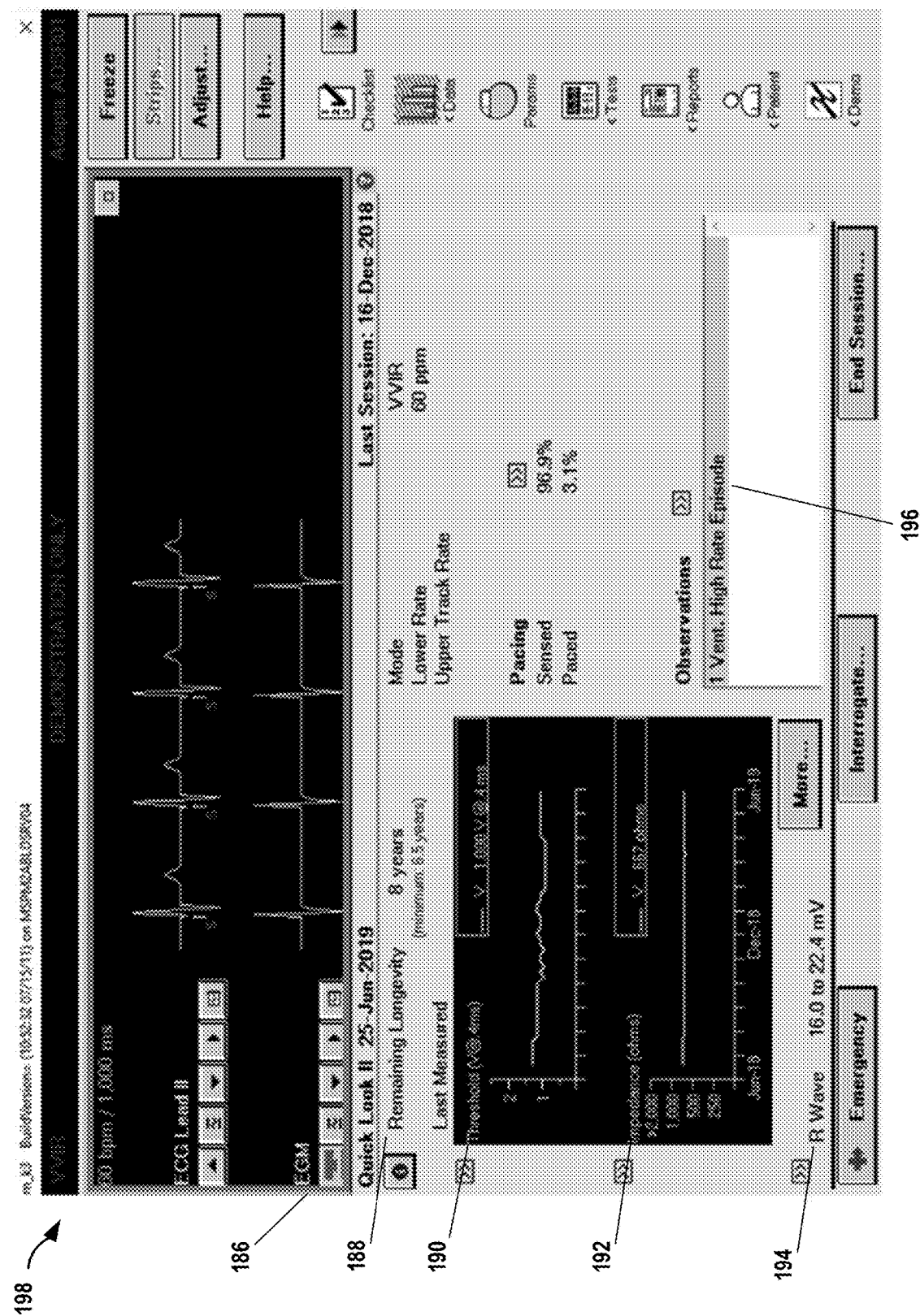
FIG. 7 illustrates an example graphical user interface for performing manual analysis of the diagnostic data of an example IMD.

In the example of FIG. 6, each value of characteristic curves 182 and 184 may have a range that is plus/minus two standard errors or a high and low value corresponding to known physical characteristics. Thus, for example the mean impedance value specified by characteristic curve 182 may have a range of plus/minus 116 Ohms at zero weeks after follow-up, a range of plus/minus 107 Ohms at two weeks after follow-up, a range of plus/minus 102 Ohms at four weeks after follow-up, and a range of plus/minus 83 Ohms at twelve weeks after follow-up. Similarly, the mean impedance value specified by characteristic curve 184 may have a range of plus/minus 114 Ohms at zero weeks after follow-up, a range of plus/minus 102 Ohms at two weeks after follow-up, a range of plus/minus 103 Ohms at four weeks after follow-up, and a range of plus/minus 85 Ohms at twelve weeks after follow-up FIG. 7 illustrates an example graphical user interface for performing manual analysis of the diagnostic data of an example IMD. As described with respect to FIGS. 4 and 5, analysis platform 130 of computing device 12 and analysis platform 170 of computing system 24 may output a user interfaces that may enable users to perform manual analysis of the diagnostic data created by IMD 10.

In the example of FIG. 7, user interface 198 may present information regarding IMD 10 that is determined based at least in part on the diagnostic data created by IMD 10 and received by computing device 12 and/or computing system 24. For example user interface 198 may include information 186 regarding the presenting rhythm of patient 4, such as the EGM of patient 4.

User interface 198 may also include the status 188 of the battery of IMD 10 (e.g., power source 54), such as in terms of the remaining longevity of the battery. User interface 198 may also include information 190 regarding the threshold of IMD 10, such as in terms of Volts. User interface 198 may also include information 192 regarding the lead impedance of the therapeutic lead in IMD 10 (e.g., leads 18, 20, and 22), such as in terms of Ohms over time. User interface 198 may also include information 194 regarding the sensing level of IMD 10, such as the ability of leads of IMD 10 to sense R-waves. User interface 198 may also include observations field 196 that enables users to input their observations.

In some examples, computing device 12 and/or computing system 24 may route the diagnostic data to one or more remote systems for manual analysis by trained technicians at a remote monitoring center. Routing the diagnostic data to one or more remote systems for manual analysis by trained technicians at a remote monitoring center may remove the burden for patient 4 to travel to a clinic or hospital in order to have the diagnostic data of IMD 10 be analyzed at the clinic or hospital and may remove the burden for clinics and hospitals to have trained technicians on-site to analyze the diagnostic data of IMD 10.

The technicians at a remote monitoring center may access the diagnostic data at one or more remote systems and may perform manual analysis of the diagnostic data to determine the operating status of IMD 10 and/or the physiological status of patient 4, such as via use of user interface 198. For example, the technicians may check for device programmed settings, special rhythm analysis requests, battery levels, therapy lead impedance values, and the like. The remote monitoring center may be staffed with technicians with different areas of expertise, such as certified cardiac technicians trained to read electrograms for arrhythmias and device technicians trained to analyze the diagnostic data of IMD 10 to determine the operating status of IMD 10. The technicians may have access to a large knowledge base including product manuals, clinical studies, and on-staff experts that the technicians may utilize to determine the operating status of IMD 10 and/or the physiological status of patient 4.

The diagnostic data may be routed to different technicians depending on the expertise of the technicians, so that EGM data may be routed to certified cardiac technicians for providing a read on the arrhythmia presence in the EGM and device data may be routed to trained device technicians for determining the operating status of IMD 10. Device technicians may follow the following technique for analyzing the device data. A device technician may, in response to receiving device data for analysis, determine the model of IMD 10 and the model of the therapy lead(s) of IMD 10 (e.g., leads 18, 20, and 22) as well as the implant date of IMD 10 in patient 4. The device technician may retrieve corresponding device manuals for device characteristics (e.g., battery depletion curves from aging tests, lead-impedance curves from clinical studies) and knowledgebase articles from the device knowledgebase database. The device technician may determine the current device values and historical trends for IMD 10 (e.g., lead impedance values over time, min and max lead impedance, battery depletion over time.).

The device technician may therefore determine the operating status of IMD 10. For example, if device technician determines that:
1) the current device-interrogation time is in the range of the published studies and the current device values are in the range of the published studies, OR the current device-interrogation time is beyond the range of the published studies and the current device values are in the extrapolated range of the published characteristics; AND
2) the current device parameter values are not more than 5% beyond the previous day's values; AND
3) the current device parameter values are not more than 10% beyond the last 10 day's average of values, if available, then the device technician may determine that IMD 10 is operating normally. In some examples, the diagnostic data may be routed to multiple device technicians to confirm the operating status of IMD 10. As described above, for example, EGM data may be routed to a cardiac technician while device data may be routed to a device technician. In response to determining the operating status of IMD 10, one or more technicians may create a report regarding the operating status of IMD 10. For example, user interface 198 may include a functionality that enables technicians to create, save, and/or print a report regarding the operating status of IMD 10.

Figure 8:
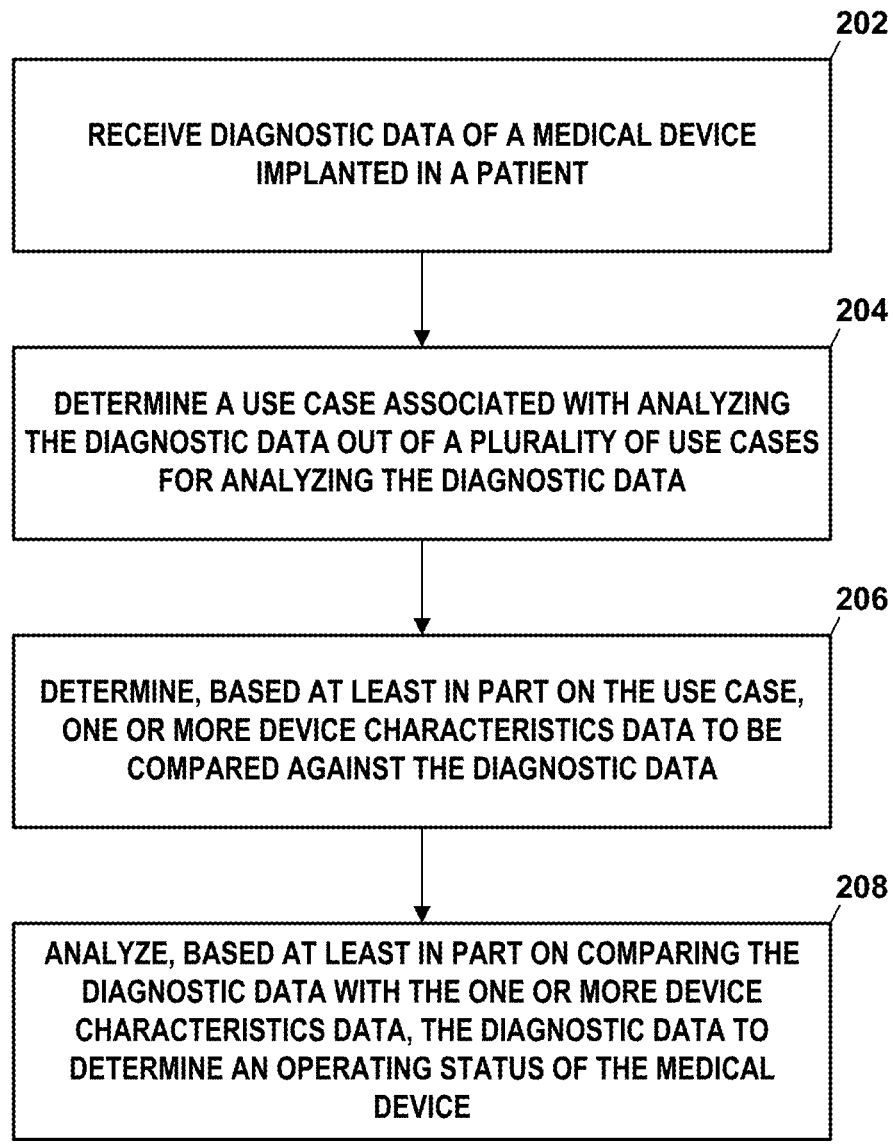
FIG. 8 is a flow diagram illustrating an example operation for monitoring an IMD

FIG. 8 is a flow diagram illustrating an example operation for monitoring an IMD. For clarity of description, the operations and techniques illustrated by FIGS. 1-7 are described as being performed by monitoring system 450, and thus by processing circuitry 402 of computing system 24. Nevertheless, those operations and techniques, and any others described herein, may be performed by processing circuitry of any one or more devices of medical device system 2, such as IMD 10, computing device 12, and computing system 24.

As shown in FIG. 8, processing circuitry 120 of computing device 12 or processing circuitry 160 of computing system 24 may receive diagnostic data of a medical device 10 implanted in a patient 4 (202). In some examples, computing device 12 may send a request for the diagnostic data to the medical device 10 and may, in response, receive the diagnostic data from the medical device 10.

Processing circuitry 120 of computing device 12 or processing circuitry 160 of computing system 24 may determine a use case associated with analyzing the diagnostic data out of a plurality of use cases for analyzing the diagnostic data (204). In some examples, the plurality of use cases for analyzing the diagnostic data include a first use case associated with next day follow-up monitoring of the medical device, a second use case associated with routine follow-up monitoring of the medical device, and a third use case associated with exception-based follow-up monitoring of the medical device.

Processing circuitry 120 of computing device 12 or processing circuitry 160 of computing system 24 may determine, at least in part on the use case, one or more device characteristics data to be compared against the diagnostic data (206).

In some examples, the one or more device characteristics data includes device characteristics data resulting from at least one of: engineering testing, bench testing, one or more clinical trials, one or more medical device product manuals, clinical best practices, or first-principles modeling of the medical device. Processing circuitry 120 of computing device 12 or processing circuitry 160 of computing system 24 may determine whether a time associated with receiving the diagnostic data of the medical device 10 is beyond a time range associated with the device characteristics data. Processing circuitry 120 of computing device 12 or processing circuitry 160 of computing system 24 may, in response to determining that the time associated with receiving the diagnostic data of the medical device 10 is beyond the time range associated with the device characteristics data: parametric fitting to determine a parametric survival curve based at least in part on the device characteristics data and extrapolate one or more values for the device characteristics data that correspond to the time associated with receiving the diagnostic data of the medical device 10.

In some examples, the one or more device characteristics data includes device characteristics data collected from a plurality of medical devices implanted in a plurality of patients. In some examples, the one or more device characteristics data includes historical device characteristics data of the medical device that are collected over time during operation of the medical device implanted in the patient.

Processing circuitry 120 of computing device 12 or processing circuitry 160 of computing system 24 may analyze, based at least in part on comparing the diagnostic data with the one or more device characteristics data, the diagnostic data to determine an operating status of the medical device 10 (208). In some examples, processing circuitry 120 of computing device 12 or processing circuitry 160 of computing system 24 may also analyze the diagnostic data to determine the patient status of the patient 4.

In some examples, processing circuitry 120 of computing device 12 or processing circuitry 160 of computing system 24 may perform one or more statistical comparisons between the diagnostic data and the one or more device characteristics data. In some examples, processing circuitry 120 of computing device 12 or processing circuitry 160 of computing system 24 may compare the diagnostic data with the one or more values for the device characteristics data that correspond to the time associated with receiving the diagnostic data of the medical device 10 to determine the operating status of the medical device 10. In some examples, processing circuitry 120 of computing device 12 or processing circuitry 160 of computing system 24 may compare the diagnostic data against at least one of: a historical maximum value of the historical device characteristics data or a historical minimum value of the historical device characteristics data to determine the operating status of the medical device 10. In some examples, processing circuitry 120 of computing device 12 or processing circuitry 160 of computing system 24 may compare the diagnostic data against an average value of the historical device characteristics data over a previous time period to determine the operating status of the medical device 10.

In some examples, the techniques of the disclosure include a system that comprises means to perform any method described herein. In some examples, the techniques of the disclosure include a computer-readable medium comprising instructions that cause processing circuitry to perform any method described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

The following examples are illustrative of the techniques described herein.

Example 1: A method comprising: receiving, by processing circuitry of a computing device, diagnostic data of a medical device implanted in a patient; determining, by the processing circuitry, a use case associated with analyzing the diagnostic data out of a plurality of use cases for analyzing the diagnostic data; determining, by the processing circuitry and based at least in part on the use case, one or more device characteristics data to be compared against the diagnostic data; and analyzing, by the processing circuitry and based at least in part on comparing the diagnostic data with the one or more device characteristics data, the diagnostic data to determine an operating status of the medical device.

Example 2: The method according to Example 1, wherein the one or more device characteristics data includes device characteristics data resulting from at least one of: engineering testing, bench testing, one or more clinical trials, one or more medical device product manuals, clinical best practices, or first-principles modeling of the medical device.

Example 3: The method according to any of Examples 1 or 2, further comprising: determining, by the processing circuitry, whether a time associated with the diagnostic data of the medical device is beyond a time range associated with the device characteristics data; and in response to determining that the time associated with the diagnostic data of the medical device is beyond the time range associated with the device characteristics data: performing, by the processing circuitry, parametric fitting to determine a parametric survival curve based at least in part on the device characteristics data, and extrapolating, by the processing circuitry, one or more values for the device characteristics data that correspond to the time associated with the diagnostic data of the medical device; wherein analyzing, based at least in part on comparing the diagnostic data with the one or more device characteristics data, the diagnostic data to determine the operating status of the medical device further comprises comparing one or more parameter values specified by the diagnostic data that are associated with one or more components of the medical device with the one or more values specified by the device characteristics data that correspond to the time associated with receiving the diagnostic data of the medical device to determine the operating status of the medical device.

Example 4: The method according to any of Examples 1-3, wherein the one or more device characteristics data includes device characteristics data collected from a plurality of medical devices implanted in a plurality of patients and wherein analyzing, based at least in part on comparing the diagnostic data with the one or more device characteristics data, the diagnostic data to determine the operating status of the medical device further comprises:

performing, by the processing circuitry, one or more statistical comparisons between the diagnostic data and the one or more device characteristics data.

Example 5: The method according to any of Examples 1-4, wherein the one or more device characteristics data includes historical device characteristics data of the medical device that are collected over time during operation of the medical device implanted in the patient.

Example 6: The method according to Example 5, wherein analyzing, based at least in part on comparing the diagnostic data with the one or more device characteristics data, the diagnostic data to determine the operating status of the medical device further comprises: comparing, by the processing circuitry, the diagnostic data against at least one of: a historical maximum value of the historical device characteristics data or a historical minimum value of the historical device characteristics data to determine the operating status of the medical device.

Example 7: The method According to any of Examples 5-6, wherein analyzing, based at least in part on comparing the diagnostic data with the one or more device characteristics data, the diagnostic data to determine the operating status of the medical device further comprises: comparing, by the processing circuitry, the diagnostic data against an average value of the historical device characteristics data over a previous time period to determine the operating status of the medical device.

Example 8: The method according to any of Examples 1-7, wherein the plurality of use cases for analyzing the diagnostic data comprise: a first use case associated with next day follow-up monitoring of the medical device; a second use case associated with routine follow-up monitoring of the medical device; and a third use case associated with exception-based follow-up monitoring of the medical device.

Example 9: The method according to any of Examples 1-8, further comprising: interrogating, by the computing device, the medical device for the diagnostic data from the medical device; wherein receiving the diagnostic data of the medical device comprises in response to interrogating the medical device, receiving, by the computing device, the diagnostic data from the medical device.

Example 10: The method according to any of Examples 1-9, wherein analyzing, based at least in part on comparing the diagnostic data with the one or more device characteristics data, the diagnostic data to determine the operating status of the medical device comprises: providing, by the processing circuitry, an analysis platform for manual analysis of the diagnostic data.

Example 11: A computing device comprising: memory; and processing circuitry in communications with the memory and configured to: receive diagnostic data of a medical device implanted in a patient; determine a use case associated with analyzing the diagnostic data out of a plurality of use cases for analyzing the diagnostic data; determine, based at least in part on the use case, one or more device characteristics data to be compared against the diagnostic data; and analyze, based at least in part on comparing the diagnostic data with the one or more device characteristics data, the diagnostic data to determine an operating status of the medical device.

Example 12: The computing device according to Example 11, wherein the one or more device characteristics data includes device characteristics data resulting from at least one of: engineering testing, bench testing, one or more clinical trials, one or more medical device product manuals, clinical best practices, or first-principles modeling of the medical device.

Example 13: The computing device according to any of Examples 11 or 12, wherein the processing circuitry is further configured to: determine whether a time associated with the diagnostic data of the medical device is beyond a time range associated with the device characteristics data; and in response to determining that the time associated with the diagnostic data of the medical device is beyond the time range associated with the device characteristics data: perform parametric fitting to determine a parametric survival curve based at least in part on the device characteristics data, and extrapolate one or more values for the device characteristics data that correspond to the time associated with the diagnostic data of the medical device; wherein the processing circuitry configured to analyze, based at least in part on comparing the diagnostic data with the one or more device characteristics data, the diagnostic data to determine the operating status of the medical device is further configured to compare one or more parameter values specified by the diagnostic data that are associated with one or more components of the medical device with the one or more values specified by the device characteristics data that correspond to the time associated with receiving the diagnostic data of the medical device to determine the operating status of the medical device.

Example 14: The computing device according to any of Examples 11-13, wherein the one or more device characteristics data includes device characteristics data collected from a plurality of medical devices implanted in a plurality of patients, and wherein the processing circuitry configured to analyze, based at least in part on comparing the diagnostic data with the one or more device characteristics data, the diagnostic data to determine the operating status of the medical device is further configured to: perform one or more statistical comparisons between the diagnostic data and the one or more device characteristics data.

Example 15: The computing device according to any of Examples 11-14, wherein the one or more device characteristics data includes historical device characteristics data of the medical device that are collected over time during operation of the medical device implanted in the patient.

Example 16: The computing device according to Example 15, wherein the processing circuitry configured to analyze, based at least in part on comparing the diagnostic data with the one or more device characteristics data, the diagnostic data to determine the operating status of the medical device is further configured to: compare the diagnostic data against at least one of: a historical maximum value of the historical device characteristics data or a historical minimum value of the historical device characteristics data to determine the operating status of the medical device.

Example 17: The computing device according to any of Examples 15-16, wherein the processing circuitry configured to analyze, based at least in part on comparing the diagnostic data with the one or more device characteristics data, the diagnostic data to determine the operating status of the medical device is further configured to: compare the diagnostic data against an average value of the historical device characteristics data over a previous time period to determine the operating status of the medical device.

Example 18: The computing device according to any of Examples 11-17, wherein the plurality of use cases for analyzing the diagnostic data comprise: a first use case associated with next day follow-up monitoring of the medical device; a second use case associated with routine follow-up monitoring of the medical device; and a third use case associated with exception-based follow-up monitoring of the medical device.

Example 19: The computing device according to any of Examples 11-18, wherein the processing circuitry is further configured to interrogate the medical device for the diagnostic data from the medical device, and wherein the processing circuitry configured to receive the diagnostic data of the medical device is further configured to receive the diagnostic data from the medical device in response to interrogating the medical device.

Example 20: A non-transitory computer-readable medium comprising instructions that, when executed by processing circuitry of a computing device, cause the computing device to: receive diagnostic data of a medical device implanted in a patient; determine a use case associated with analyzing the diagnostic data out of a plurality of use cases for analyzing the diagnostic data; determine, based at least in part on the use case, one or more device characteristics data to be compared against the diagnostic data; and analyze, based at least in part on comparing the diagnostic data with the one or more device characteristics data, the diagnostic data to determine an operating status of the medical device.

Various examples have been described. These and other examples are within the scope of the following claims.

What is claimed is:

1. A method comprising:
    receiving, by processing circuitry of a computing device, diagnostic data of a medical device implanted in a patient;
    determining, by the processing circuitry, a use case associated with analyzing the diagnostic data out of a plurality of use cases for analyzing the diagnostic data, wherein the plurality of use cases include post-surgical follow-up monitoring of the medical device, routine follow-up monitoring of the medical device, and exception-based follow-up monitoring of the medical device;
    storing, by the processing circuitry in memory of the computing device, a value indicative of whether to route the diagnostic data to a computing system for analysis;
    in response to determining, based on the value stored in the memory, to refrain from routing the diagnostic data to the computing system, determining, by the processing circuitry and based at least in part on the use case, one or more device characteristics data to be compared against the diagnostic data; and
    analyzing, by the processing circuitry and based at least in part on comparing the diagnostic data with the one or more device characteristics data, the diagnostic data to determine an operating status of the medical device.

2. The method of claim 1, wherein the one or more device characteristics data includes device characteristics data resulting from at least one of: engineering testing, bench testing, one or more clinical trials, one or more medical device product manuals, clinical best practices, or first-principles modeling of the medical device.

3. The method of claim 2, further comprising:
    determining, by the processing circuitry, whether a time associated with the diagnostic data of the medical device is beyond a time range associated with the device characteristics data; and
    in response to determining that the time associated with the diagnostic data of the medical device is beyond the time range associated with the device characteristics data:
        performing, by the processing circuitry, parametric fitting to determine a parametric survival curve based at least in part on the device characteristics data, and
        extrapolating, by the processing circuitry, one or more values for the device characteristics data that correspond to the time associated with the diagnostic data of the medical device;
    wherein analyzing, based at least in part on comparing the diagnostic data with the one or more device characteristics data, the diagnostic data to determine the operating status of the medical device further comprises comparing one or more parameter values specified by the diagnostic data that are associated with one or more components of the medical device with the one or more values specified by the device characteristics data that correspond to the time associated with receiving the diagnostic data of the medical device to determine the operating status of the medical device.

4. The method of claim 1, wherein the one or more device characteristics data includes device characteristics data collected from a plurality of medical devices implanted in a plurality of patients, and wherein analyzing, based at least in part on comparing the diagnostic data with the one or more device characteristics data, the diagnostic data to determine the operating status of the medical device further comprises:
    performing, by the processing circuitry, one or more statistical comparisons between the diagnostic data and the one or more device characteristics data.

5. The method of claim 1, wherein the one or more device characteristics data includes historical device characteristics data of the medical device that are collected over time during operation of the medical device implanted in the patient.

6. The method of claim 5, wherein analyzing, based at least in part on comparing the diagnostic data with the one or more device characteristics data, the diagnostic data to determine the operating status of the medical device further comprises:
    comparing, by the processing circuitry, the diagnostic data against at least one of: a historical maximum value of the historical device characteristics data or a historical minimum value of the historical device characteristics data to determine the operating status of the medical device.

7. The method of claim 5, wherein analyzing, based at least in part on comparing the diagnostic data with the one or more device characteristics data, the diagnostic data to determine the operating status of the medical device further comprises:
    comparing, by the processing circuitry, the diagnostic data against an average value of the historical device characteristics data over a previous time period to determine the operating status of the medical device.

8. The method of claim 1, further comprising:
    interrogating, by the computing device, the medical device for the diagnostic data from the medical device;
    wherein receiving the diagnostic data of the medical device comprises in response to interrogating the medical device, receiving, by the computing device, the diagnostic data from the medical device.

9. The method of claim 1, wherein analyzing, based at least in part on comparing the diagnostic data with the one or more device characteristics data, the diagnostic data to determine the operating status of the medical device comprises:

providing, by the processing circuitry, an analysis platform for manual analysis of the diagnostic data.

10. A computing device comprising:
memory; and
processing circuitry in communications with the memory and configured to:
   receive diagnostic data of a medical device implanted in a patient;
   determine a use case associated with analyzing the diagnostic data out of a plurality of use cases for analyzing the diagnostic data, wherein the plurality of use cases include next day follow-up monitoring of the medical device, routine follow-up monitoring of the medical device, and exception-based follow-up monitoring of the medical device;
   store, in the memory of the computing device, a value indicative of whether to route the diagnostic data to a computing system for analysis;
   in response to determining, based on the value stored in the memory, to refrain from routing the diagnostic data to the computing system, determine, based at least in part on the use case, one or more device characteristics data to be compared against the diagnostic data;
   analyze, based at least in part on comparing the diagnostic data with the one or more device characteristics data, the diagnostic data to determine an operating status of the medical device; and
   in response to determining, based on the value stored in the memory, to route the diagnostic data to the computing system, sending the diagnostic data to the remote computing system.

11. The computing device of claim 10, wherein the one or more device characteristics data includes device characteristics data resulting from at least one of: engineering testing, bench testing, one or more clinical trials, one or more medical device product manuals, clinical best practices, or first-principles modeling of the medical device.

12. The computing device of claim 11, wherein the processing circuitry is further configured to:
   determine whether a time associated with the diagnostic data of the medical device is beyond a time range associated with the device characteristics data; and
   in response to determining that the time associated with the diagnostic data of the medical device is beyond the time range associated with the device characteristics data:
      perform parametric fitting to determine a parametric survival curve based at least in part on the device characteristics data, and
      extrapolate one or more values for the device characteristics data that correspond to the time associated with the diagnostic data of the medical device;
   wherein the processing circuitry configured to analyze, based at least in part on comparing the diagnostic data with the one or more device characteristics data, the diagnostic data to determine the operating status of the medical device is further configured to compare one or more parameter values specified by the diagnostic data that are associated with one or more components of the medical device with the one or more values specified by the device characteristics data that correspond to the time associated with receiving the diagnostic data of the medical device to determine the operating status of the medical device.

13. The computing device of claim 10, wherein the one or more device characteristics data includes device characteristics data collected from a plurality of medical devices implanted in a plurality of patients, and wherein the processing circuitry configured to analyze, based at least in part on comparing the diagnostic data with the one or more device characteristics data, the diagnostic data to determine the operating status of the medical device is further configured to perform or more statistical comparisons between the diagnostic data and the one or more device characteristics data.

14. The computing device of claim 10, wherein the one or more device characteristics data includes historical device characteristics data of the medical device that are collected over time during operation of the medical device implanted in the patient.

15. The computing device of claim 14, wherein the processing circuitry configured to analyze, based at least in part on comparing the diagnostic data with the one or more device characteristics data, the diagnostic data to determine the operating status of the medical device is further configured to:
   compare the diagnostic data against at least one of: a historical maximum value of the historical device characteristics data or a historical minimum value of the historical device characteristics data to determine the operating status of the medical device.

16. The computing device of claim 14, wherein the processing circuitry configured to analyze, based at least in part on comparing the diagnostic data with the one or more device characteristics data, the diagnostic data to determine the operating status of the medical device is further configured to:
   compare the diagnostic data against an average value of the historical device characteristics data over a previous time period to determine the operating status of the medical device.

17. The computing device of claim 10, wherein the processing circuitry is further configured to interrogate the medical device for the diagnostic data from the medical device, and wherein the processing circuitry configured to receive the diagnostic data of the medical device is further configured to receive the diagnostic data from the medical device in response to interrogating the medical device.

18. A non-transitory computer-readable medium comprising instructions that, when executed by processing circuitry of a computing device, cause the computing device to:
   receive diagnostic data of a medical device implanted in a patient;
   determine a use case associated with analyzing the diagnostic data out of a plurality of use cases for analyzing the diagnostic data, wherein the plurality of use cases include post-surgical follow-up monitoring of the medical device, routine follow-up monitoring of the medical device, and exception-based follow-up monitoring of the medical device;
   determine, based on the use case associated with analyzing the diagnostic data, a value indicative of whether to route the diagnostic data to the computing system for analysis;
   store, in memory of the computing device, the value indicative of whether to route the diagnostic data to a computing system for analysis;
   in response to determining, based on the value stored in the memory, to refrain from routing the diagnostic data to the computing system, determine, based at least in part on the use case, one or more device characteristics data to be compared against the diagnostic data;

analyze, based at least in part on comparing the diagnostic data with the one or more device characteristics data, the diagnostic data to determine an operating status of the medical device; and in response to determining, based on the value stored in the memory, to route the diagnostic data to the computing system, sending the diagnostic data to the remote computing system.

19. The method of claim 1, further comprising:

determining, by the processing circuitry and based on the use case associated with analyzing the diagnostic data, the value indicative of whether to route the diagnostic data to the computing system for analysis.

20. The method of claim 1, further comprising:

in response to determining, based on the value stored in the memory, to route the diagnostic data to the computing system, sending, by the processing circuitry, the diagnostic data to the computing system.

21. The computing device of claim 10, wherein the processing circuitry is further configured to:

determine, based on the use case associated with analyzing the diagnostic data, the value indicative of whether to route the diagnostic data to the computing system for analysis.

22. The computing device of claim 21, wherein the next day follow-up monitoring of the medical device is indicative of not routing the diagnostic data to the computing system for analysis, and wherein the routine follow-up monitoring of the medical device and the exception-based follow-up monitoring of the medical device are indicative of routing the diagnostic data to the computing system for analysis.

\* \* \* \* \*